United States Patent [19]
Kamboj et al.

[11] Patent Number: 6,013,768
[45] Date of Patent: Jan. 11, 2000

[54] KAINATE-BINDING HUMAN CNS RECEPTORS OF THE EAA1 FAMILY

[75] Inventors: Rajender Kamboj, Mississauga; Stephen L. Nutt, Etobicoke; Lee Shekter, Toronto; Michael A. Wosnick, Thornhill, all of Canada

[73] Assignee: Allelix Biopharmaceuticals, Inc., Mississauga, Canada

[21] Appl. No.: 08/789,478

[22] Filed: Jan. 27, 1997

Related U.S. Application Data

[62] Division of application No. 08/416,523, Apr. 3, 1995, Pat. No. 5,616,481, which is a continuation of application No. 08/091,441, Jul. 15, 1993, abandoned, which is a division of application No. 08/185,232, Jan. 24, 1994, Pat. No. 5,576,205, which is a continuation of application No. 07/750,090, Aug. 26, 1991, abandoned.

[51] Int. Cl.$^7$ .......................... C07K 14/705; C12N 15/12
[52] U.S. Cl. .......................... 530/350; 530/300; 530/395; 435/69.1; 536/23.5
[58] Field of Search .................................... 530/350, 300, 530/395; 435/69.1; 536/23.5

[56] References Cited

FOREIGN PATENT DOCUMENTS

91/06648    5/1991    WIPO.

OTHER PUBLICATIONS

Lewin, Science, 237, 1570, Sep. 1987.
Harlow et al., Antibodies, 72–76, 1988.
Reeck et al., Cell, 50, 667, Aug. 1987.
Hollmann et al., Nature 1989, 342:643.
Keinanen et al., Science 1990, 249:556.
Boulter et al., Science 1990, 249:1033.
Bettler et al., Neuron 1990, 5:583.
Sommer et al., Science 1990, 249:1580.
Monyer et al., Neuron 1991, 6:799.
Nakanishi et al., Neuron 1990, 5:569.
Hollmann et al., Science 1991, 252:851.
Verdoorn et al., Science 1991, 252:1715.
Egebjerg et al., Nature 1991, 351:745.
Wada et al., Nature 1991, 342:684.
Gregor et al., Nature 1989, 342:689.
Werner et al., Nature 1991, 351:742.
Barnett et al., Nucleic Acids Res. 1990, 18(10):3094.
S.V. Suggs et al., PNAS 78(11):6613–6617 (1981).
W. Sun et al., "Molecular Cloning, Chromosomal Mapping, and Functional Expression of Human Brain Glutamate Receptors", Proc. Natl. Acad. Sci. USA, vol. 89, pp. 1443–1447, Feb. 1992.
C. Puckett et al., "Molecular Cloning and Chromosomal Localization of One of the Human Glutamate Receptor Genes", Proc. Natl. Acad. Sci. USA, vol. 88, pp. 7557–7561, Sep. 1991.

*Primary Examiner*—Sally P. Teng
*Attorney, Agent, or Firm*—Foley & Lardner

[57] ABSTRACT

Neurotransmission by excitatory amino acids (EAAs) such as glutamate is mediated via membrane-bound surface receptors. DNA coding for one family of these receptors, of the kainate binding type of EAA receptors, has now been isolated and the receptor protein characterized. Herein described art recombinant cell lines which produce the EAA receptor as a heterologous membrane-bound product. Also described are related aspects of the invention, which are of commercial significance. Included is use of the cell lines as a tool for discovery of compounds which modulate EAA receptor stimulation.

5 Claims, 14 Drawing Sheets

(LINEAR) MAP OF HumEAAIa      FIG.1(a)

```
      EcoRI
      |
  1   GAATTCCCTGAGTGCCTACTATGTGCCAGCCTGTGCTAGGCACTGAGGACACAGGTGGAA   60
      ------------------------------------------------------------
      CTTAAGGGACTCACGGATGATACACGGTCGGACACGATCCGTGACTCCTGTGTCCACCTT

HphI
                         |
  61  AAGCCCGAATTGCTCCCTGCTCTCCTGGCGCTCATCACCCCGGAGAGTTATGTCATGCCC   120
      ------------------------------------------------------------
      TTCGGGCTTAACGAGGGACGAGAGGACCGCGAGTAGTGGGGCCTCTCAATACAGTACGGG

121  AGGCCAGCAGGGGGCTCCATGAGGATTCATAGAAGATGCCCCGCGTCTCGGCGCCTTTGG   180
      ------------------------------------------------------------
      TCCGGTCGTCCCCCGAGGTACTCCTAAGTATCTTCTACGGGGCGCAGAGCCGCGGAAACC

M   P   R   V   S   A   P   L   V
                                           -20                  -15
                                         PstI
                                         |
 181  TGCTGCTTCCTGCGTGGCTCGTGATGGTCGCCTGCAGCCCGCACTCCTTGAGGATCGCTG   240
      ------------------------------------------------------------
      ACGACGAAGGACGCACCGAGCACTACCAGCGGACGTCGGGCGTGAGGAACTCCTAGCGAC

L   L   P   A   W   L   V   M   V   A   C   S   P   H   S   L   R   I   A   A   9
      -10              -5                    | Mature N-terminal NcoI                              HphI
                        |                                 |
 241  CTATCTTGGACGACCCCATGGAGTGCAGCAGAGGGGAGCGGCTCTCCATCACCCTGGCCA   300
      ------------------------------------------------------------
      GATAGAACCTGCTGGGGTACCTCACGTCGTCTCCCCTCGCCGAGAGGTAGTGGGACCGGT 10   I   L   D   D   P   M   E   C   S   R   G   E   R   L   S   I   T   L   A   K   29

301  AGAACCGCATCAACCGCGCTCCTGAGAGGCTGGGCAAGGCCAAGGTCGAAGTGGACATCT   360
      ------------------------------------------------------------
      TCTTGGCGTAGTTGGCGCGAGGACTCTCCGACCCGTTCCGGTTCCAGCTTCACCTGTAGA

30   N   R   I   N   R   A   P   E   R   L   G   K   A   K   V   E   V   D   I   F
                                                                      PstI
                                                                      |
 361  TTGAGCTTCTCAGAGACAGCGAGTACGAGACTGCAGAAACCATGTGTCAGATCCTCCCCA   420
      ------------------------------------------------------------
      AACTCGAAGAGTCTCTGTCGCTCATGCTCTGACGTCTTTGGTACACAGTCTAGGAGGGGT

50   E   L   L   R   D   S   E   Y   E   T   A   E   T   M   C   Q   I   L   P   K   49

421  AGGGGGTGGTCGCTGTCCTCGGACCATCGTCCAGCCCAGCCTCCAGCTCCATCATCAGCA   480
      ------------------------------------------------------------
      TCCCCCACCAGCGACAGGAGCCTGGTAGCAGGTCGGGTCGGAGGTCGAGGTAGTAGTCGT

```
481  ACATCTGTGGAGAGAAGGAGGTCCCTCACTTCAAAGTGGCCCCAGAGGAGTTCGTCAAGT  540
     TGTAGACACCTCTCTTCCTCCAGGGAGTGAAGTTTCACCGGGGTCTCCTCAAGCAGTTCA
 90   I  C  G  E  K  E  V  P  H  F  K  V  A  P  E  E  F  V  K  F  109

541  TCCAGTTCCAGAGATTCACAACCCTGAACCTCCACCCCAGCAACACTGACATCAGCGTGG  600
     AGGTCAAGGTCTCTAAGTGTTGGGACTTGGAGGTGGGGTCGTTGTGACTGTAGTCGCACC
110   Q  F  Q  R  F  T  T  L  N  L  H  P  S  N  T  D  I  S  V  A  129

BamHI         XmnI
601  CTGTAGCTGGGATCCTGAACTTCTTCAACTGCACCACCGCCTGCCTCATCTGTGCCAAAG  660
     GACATCGACCCTAGGACTTGAAGAAGTTGACGTGGTGGCGGACGGAGTAGACACGGTTTC
130   V  A  G  I  L  N  F  F  N  C  T  T  A  C  L  I  C  A  K  A  149

661  CAGAATGCCTTTTAAACCTAGAGAAGCTGCTCCGGCAATTCCTTATCTCCAAGGACACGC  720
     GTCTTACGGAAAATTTGGATCTCTTCGACGAGGCCGTTAAGGAATAGAGGTTCCTGTGCG
150   E  C  L  L  N  L  E  K  L  L  R  Q  F  L  I  S  K  D  T  L  169

721  TGTCCGTCCGCATGCTGGATGACACCCGGGACCCCACCCCGCTCCTCAAGGAGATCCGGG  780
     ACAGGCAGGCGTACGACCTACTGTGGGCCCTGGGGTGGGGCGAGGAGTTCCTCTAGGCCC
170   S  V  R  M  L  D  D  T  R  D  P  T  P  L  L  K  E  I  R  D  189

781  ACGACAAGACCGCCACCATCATCATCCACGCCAACGCCTCCATGTCCCACACCATCCTCC  840
     TGCTGTTCTGGCGGTGGTAGTAGTAGGTGCGGTTGCGGAGGTACAGGGTGTGGTAGGAGG
190   D  K  T  A  T  I  I  I  H  A  N  A  S  M  S  H  T  I  L  L  209

841  TGAAGGCAGCCGAACTTGGGATGGTGTCAGCCTATTACACATACATCTTCACTAATCTGG  900
     ACTTCCGTCGGCTTGAACCCTACCACAGTCGGATAATGTGTATGTAGAAGTGATTAGACC
210   K  A  A  E  L  G  M  V  S  A  Y  Y  T  Y  I  F  T  N  L  E  229

901  AGTTCTCACTCCAGAGAACGGACAGCCTTGTGGATGATCGTGTCAACATCCTGGGATTTT  960
     TCAAGAGTGAGGTCTCTTGCCTGTCGGAACACCTACTAGCACAGTTGTAGGACCCTAAAA
230   F  S  L  Q  R  T  D  S  L  V  D  D  R  V  N  I  L  G  F  S  249

961  CCATTTTCAACCAATCCCATGCTTTCTTCCAAGAGTTTGCCCAGAGCCTCAACCAGTCCT  1020
     GGTAAAAGTTGGTTAGGGTACGAAAGAAGGTTCTCAAACGGGTCTCGGAGTTGGTCAGGA
250   I  F  N  Q  S  H  A  F  F  Q  E  F  A  Q  S  L  N  Q  S  W  269
```

FIG. I(c)

```
1021 GGCAGGAGAACTGTGACCATGTGCCCTTCACTGGGCCTGCGCTCTCCTCGGCCCTGCTGT 1080
     CCGTCCTCTTGACACTGGTACACGGGAAGTGACCCGGACGCGAGAGGAGCCGGGACGACA

270   Q  E  N  C  D  H  V  P  F  T  G  P  A  L  S  S  A  L  L  F   289
                                    HphI

1081 TTGATGCTGTCTATGCTGTGGTGACTGCGGTGCAGGAACTGAACCGGAGCCAAGAGATCG 1140
     AACTACGACAGATACGACACCACTGACGCCACGTCCTTGACTTGGCCTCGGTTCTCTAGC

290   D  A  V  Y  A  V  V  T  A  V  Q  E  L  N  R  S  Q  E  I  G   309

1141 GCGTGAAGCCCTTGTCCTGCGGCTCGGCCCAGATCTGGCAGCACGGCACCAGCCTCATGA 1200
     CGCACTTCGGGAACAGGACGCCGAGCCGGGTCTAGACCGTCGTGCCGTGGTCGGAGTACT

310   V  K  P  L  S  C  G  S  A  Q  I  W  Q  H  G  T  S  L  M  N   329
                                                          EcoRI

1201 ACTACCTGCGCATGGTAGAATTGGAAGGTCTTACCGGCCACATTGAATTCAACAGCAAAG 1260
     TGATGGACGCGTACCATCTTAACCTTCCAGAATGGCCGGTGTAACTTAAGTTGTCGTTTC

330   Y  L  R  M  V  E  L  E  G  L  T  G  H  I  E  F  N  S  K  G   349

1261 GCCAGAGGTCCAACTACGCTTTGAAAATCTTACAGTTCACAAGGAATGGTTTTCGGCAGA 1320
     CGGTCTCCAGGTTGATGCGAAACTTTTAGAATGTCAAGTGTTCCTTACCAAAAGCCGTCT

350   Q  R  S  N  Y  A  L  K  I  L  Q  F  T  R  N  G  F  R  Q  I   369

1321 TCGGCCAGTGGCACGTGGCAGAGGGCCTCAGCATGGACAGCCACCTCTATGCCTCCAACA 1380
     AGCCGGTCACCGTGCACCGTCTCCCGGAGTCGTACCTGTCGGTGGAGATACGGAGGTTGT

370   G  Q  W  H  V  A  E  G  L  S  M  D  S  H  L  Y  A  S  N  I   389
                                HphI

1381 TCTCGGACACTCTCTTCAACACCACCCTGGTCGTCACCACCATCCTGGAAAACCCATATT 1440
     AGAGCCTGTGAGAGAAGTTGTGGTGGGACCAGCAGTGGTGGTAGGACCTTTTGGGTATAA

390   S  D  T  L  F  N  T  T  L  V  V  T  T  I  L  E  N  P  Y  L   409

1441 TAATGCTGAAGGGGAACCACCAGGAGATGGAAGGCAATGACCGCTACGAGGGCTTCTGTG 1500
     ATTACGACTTCCCCTTGGTGGTCCTCTACCTTCCGTTACTGGCGATGCTCCCGAAGACAC

410   M  L  K  G  N  H  Q  E  M  E  G  N  D  R  Y  E  G  F  C  V   429

1501 TGGACATGCTCAAGGAGCTGGCAGAGATCCTCCGATTCAACTACAAGATCCGCCTGGTTG 1560
     ACCTGTACGAGTTCCTCGACCGTCTCTAGGAGGCTAAGTTGATGTTCTAGGCGGACCAAC

```
1561 GGGATGGCGTGTACGGCGTTCCCGAGGCCAACGGCACCTGGACGGGAATGGTCGGGGAGC 1620
     CCCTACCGCACATGCCGCAAGGGCTCCGGTTGCCGTGGACCTGCCCTTACCAGCCCCTCG

450   D  G  V  Y  G  V  P  E  A  N  G  T  W  T  G  M  V  G  E  L  469

HphI
                                     |
1621 TGATCGCTAGGAAAGCAGATCTGGCTGTGGCAGGCCTCACCATTACAGCTGAACGGGAGA 1680
     ACTAGCGATCCTTTCGTCTAGACCGACACCGTCCGGAGTGGTAATGTCGACTTGCCCTCT

470   I  A  R  K  A  D  L  A  V  A  G  L  T  I  T  A  E  R  E  K  489

HphI
                       |
1681 AGGTGATTGATTTCTCTAAGCCATTCATGACTCTGGGAATTAGCATTCTTTACCGCATTC 1740
     TCCACTAACTAAAGAGATTCGGTAAGTACTGAGACCCTTAATCGTAAGAAATGGCGTAAG

490   V  I  D  F  S  K  P  F  M  T  L  G  I  S  I  L  Y  R  I  H  509

1741 ATATGGGACGCAAACCCGGCTATTTCTCCTTCCTGGACCCATTTTCTCCGGGCGTCTGGC 1800
     TATACCCTGCGTTTGGGCCGATAAAGAGGAAGGACCTGGGTAAAAGAGGCCCGCAGACCG

510   M  G  R  K  P  G  Y  F  S  F  L  D  P  F  S  P  G  V  W  L  529

1801 TCTTCATGCTTCTAGCCTATCTGGCCGTCAGCTGTGTCCTCTTCCTGGTGGCTCGGTTGA 1860
     AGAAGTACGAAGATCGGATAGACCGGCAGTCGACACAGGAGAAGGACCACCGAGCCAACT

530   F  M  L  L  A  Y  L  A  V  S  C  V  L  F  L  V  A  R  L  T  549

1861 CGCCCTACGAGTGGTACAGCCCACACCCATGTGCCCAGGGCCGGTGCAACCTCCTGGTGA 1920
     GCGGGATGCTCACCATGTCGGGTGTGGGTACACGGGTCCCGGCCACGTTGGAGGACCACT

550   P  Y  E  W  Y  S  P  H  P  C  A  Q  G  R  C  N  L  L  V  N  569
            HphI
             |
1921 ACCAGTACTCCCTGGGCAACAGCCTCTGGTTTCCGGTCGGGGGGTTCATGCAGCAGGGCT 1980
     TGGTCATGAGGGACCCGTTGTCGGAGACCAAAGGCCAGCCCCCAAGTACGTCGTCCCGA

570   Q  Y  S  L  G  N  S  L  W  F  P  V  G  G  F  M  Q  Q  G  S  589

1981 CCACCATCGCCCCTCGCGCCTTATCCACCCGCTGTGTCAGTGGCGTCTGGTGGGCATTCA 2040
     GGTGGTAGCGGGGAGCGCGGAATAGGTGGGCGACACAGTCACCGCAGACCACCCGTAAGT

590   T  I  A  P  R  A  L  S  T  R  C  V  S  G  V  W  W  A  F  T  609

2041 CGCTGATCATCATCTCATCCTACACGGCCAACCTGGCAGCCTTCCTGACCGTGCAGCGCA 2100
     GCGACTAGTAGTAGAGTAGGATGTGCCGGTTGGACCGTCGGAAGGACTGGCACGTCGCGT

```
2101  TGGATGTGCCCATTGAGTCAGTGGATGACCTGGCTGACCAGACCGCCATTGAATATGGCA  2160
      ACCTACACGGGTAACTCAGTCACCTACTGGACCGACTGGTCTGGCGGTAACTTATACCGT

630    D  V  P  I  E  S  V  D  D  L  A  D  Q  T  A  I  E  Y  G  T 649

2161  CAATTCACGGAGGCTCCAGCATGACCTTCTTCCAAAATTCCCGCTACCAGACCTACCAAC  2220
      GTTAAGTGCCTCCGAGGTCGTACTGGAAGAAGGTTTTAAGGGCGATGGTCTGGATGGTTG

650    I  H  G  G  S  S  M  T  F  F  Q  N  S  R  Y  Q  T  Y  Q  R 669

2221  GCATGTGGAATTACATGTATTCCAAGCAGCCCAGCGTGTTCGTGAAGAGCACAGAGGAGG  2280
      CGTACACCTTAATGTACATAAGGTTCGTCGGGTCGCACAAGCACTTCTCGTGTCTCCTCC

670    M  W  N  Y  M  Y  S  K  Q  P  S  V  F  V  K  S  T  E  E  G 689

EcoRI
                                         |
2281  GAATCGCCAGGGTGTTGAATTCCAACTACGCCTTCCTCCTGGAATCCACCATGAACGAGT  2340
      CTTAGCGGTCCCACAACTTAAGGTTGATGCGGAAGGAGGACCTTAGGTGGTACTTGCTCA

690    I  A  R  V  L  N  S  N  Y  A  F  L  L  E  S  T  M  N  E  Y 709

2341  ACTATCGGCAGCGAAACTGCAACCTCACTCAGATTGGGGGCCTGCTGGACACCAAGGGCT  2400
      TGATAGCCGTCGCTTTGACGTTGGAGTGAGTCTAACCCCCGGACGACCTGTGGTTCCCGA

710    Y  R  Q  R  N  C  N  L  T  Q  I  G  G  L  L  D  T  K  G  Y 729

2401  ATGGGATTGGCATGCCAGTCGGCTCGGTTTTCCGGGACGAGTTTGATCTGGCCATTCTCC  2460
      TACCCTAACCGTACGGTCAGCCGAGCCAAAAGGCCCTGCTCAAACTAGACCGGTAAGAGG

730    G  I  G  M  P  V  G  S  V  F  R  D  E  F  D  L  A  I  L  Q 749
            PstI
             |
2461  AGCTGCAGGAGAACAACCGCCTGGAGATCCTGAAGCGCAAATGGTGGGAAGGAGGGAAGT  2520
      TCGACGTCCTCTTGTTGGCGGACCTCTAGGACTTCGCGTTTACCACCCTTCCTCCCTTCA

750    L  Q  E  N  N  R  L  E  I  L  K  R  K  W  W  E  G  G  K  C 769
                                                      SspI
                                                        |
2521  GCCCCAAGGAGGAAGATCACAGAGCTAAAGGCCTGGGAATGGAGAATATTGGTGGAATCT  2580
      CGGGGTTCCTCCTTCTAGTGTCTCGATTTCCGGACCCTTACCTCTTATAACCACCTTAGA

770    P  K  E  E  D  H  R  A  K  G  L  G  M  E  N  I  G  G  I  F 789

2581  TTGTGGTTCTTATTTGTGGCTTAATCGTGGCCATTTTTATGGCTATGTTGGAGTTTTTAT  2640
      AACACCAAGAATAAACACCGAATTAGCACCGGTAAAAATACCGATACAACCTCAAAAATA

```
2641 GGACTCTCAGACACTCAGAAGCAACTGAGGTGTCCGTCTGCCAGGAGATGGTGACCGAGC 2700
     CCTGAGAGTCTGTGAGTCTTCGTTGACTCCACAGGCAGACGGTCCTCTACCACTGGCTCG
810    T  L  R  H  S  E  A  T  E  V  S  V  C  Q  E  M  V  T  E  L 829

HphI
            |
2701 TGCGCAGCATTATCCTGTGTCAGGACAGTATCCACCCCCGCCGGCGGCGCGCCGCAGTCC 2760
     ACGCGTCGTAATAGGACACAGTCCTGTCATAGGTGGGGGCGGCCGCCGCGCGGCGTCAGG
830    R  S  I  I  L  C  Q  D  S  I  H  P  R  R  R  R  A  A  V  P 849

2761 CGCCGCCCCGGCCCCCCATCCCCGAGGAGCGCCGACCGCGGGGCACGGCGACGCTCAGCA 2820
     GCGGCGGGGCCGGGGGGTAGGGGCTCCTCGCGGCTGGCGCCCCGTGCCGCTGCGAGTCGT
850    P  P  R  P  P  I  P  E  E  R  R  P  R  G  T  A  T  L  S  N 869

2821 ACGGGAAGCTGTGCGGGGCAGGGGAGCCCGACCAGCTCGCGCAGAGACTGGCGCAGGAGG 2880
     TGCCCTTCGACACGCCCCGTCCCCTCGGGCTGGTCGAGCGCGTCTCTGACCGCGTCCTCC
870    G  K  L  C  G  A  G  E  P  D  Q  L  A  Q  R  L  A  Q  E  A 889

2881 CCGCCCTGGTGGCCCGCGGCTGCACGCACATCCGCGTCTGCCCCGAGTGCCGCCGCTTCC 2940
     GGCGGGACCACCGGGCGCCGACGTGCGTGTAGGCGCAGACGGGGCTCACGGCGGCGAAGG
890    A  L  V  A  R  G  C  T  H  I  R  V  C  P  E  C  R  R  F  Q 909

2941 AGGGCCTGCGGGCACGGCCGTCGCCCGCCCGCAGCGAGGAGAGCCTGGAGTGGGAGAAAA 3000
     TCCCGGACGCCCGTGCCGGCAGCGGGCGGGCGTCGCTCCTCTCGGACCTCACCCTCTTTT
910    G  L  R  A  R  P  S  P  A  R  S  E  E  S  L  E  W  E  K  T 929

3001 CCACCAACAGCAGCGAGCCCGAGTAGTCCCGGAGGCCACAGGACGCGCAGAGGCCGGGCG 3060
     GGTGGTTGTCGTCGCTCGGGCTCATCAGGGCCTCCGGTGTCCTGCGCGTCTCCGGCCCGC
930    T  N  S  S  E  P  E 936 *

3061 GGGCGGGAGGGGAGGGGCGGGGCGGGCGCTGCTGTCAGCCGCCAGCCGGAACTTGTACAG 3120
     CCCGCCCTCCCCTCCCCGCCCCGCCCGCGACGACAGTCGGCGGTCGGCCTTGAACATGTC
         SalI                          BamHI
          |                              |
3121 CGTCGACACCTCTCCAGATTTCGGATCCAGTCACTTTTCAAAAAGATCAAGGAGCCTGAC 3180
     GCAGCTGTGGAGAGGTCTAAAGCCTAGGTCAGTGAAAAGTTTTTCTAGTTCCTCGGACTG

3181 GCCCCAGCCAGAGACCGCGCCCGGTCAGGGAGCAGGGTCCACCCGGAAACGTTGCACCCA 3240
     CGGGGTCGGTCTCTGGCGCGGGCCAGTCCCTCGTCCCAGGTGGGCCTTTGCAACGTGGGT
```

FIG. I(g)

```
3241 AAGGGCAAAGGACGGCCCTCCCTCCTGGGCACAAGGACCCATCTTCTCCCAGTGGGTCTT 3300
     TTCCCGTTTCCTGCCGGGAGGGAGGTCCCGTGTTCCTGGGTAGAAGAGGGTCACCCAGAA

3301 TCCCTCTCGCCAAAATAACAAGAGTATAGGGTGGGGGGTCCCTACCCAGACCAGTCCAAT 3360
     AGGGAGAGCGGTTTTATTGTTCTCATATCCCACCCCCCAGGGATGGGTCTGGTCAGGTTA

3361 GAATTGGTGGAATCATCAGTTGAATTTCCCCCTAGTCAGGGGCCAATGTACCCTCCGTCT 3420
     CTTAACCACCTTAGTAGTCAACTTAAAGGGGGATCAGTCCCCGGTTACATGGGAGGCAGA
                                                Xmn I
3421 AGTTCTTACAGAAAAAAAAAAAAATTAAACAGGGAAGTTTTTCTTTTCTGGATTTGTATA 3480
     TCAAGAATGTCTTTTTTTTTTTTAATTTGTCCCTTCAAAAAGAAAAGACCTAAACATAT

3481 TTTTTGTTAATGTTCTTTTCCCTTTTCTTTCCTCCTCTCCTTTTCTTCTTTGTCATCTTC 3540
     AAAAACAATTACAAGAAAAGGGAAAAGAAAGGAGGAGAGGAAAAGAAGAAACAGTAGAAG

3541 TCAGTCCTGTTAATTTGTTTTGTGTTTTTTGGAGGGGGAGGCTGGGTTAGGGAATGGAAG 3600
     AGTCAGGACAATTAAACAAAACACAAAAAAACCTCCCCCTCCGACCCAATCCCTTACCTTC
                                            Ssp I
3601 CCTAAATAATCCCTATTTCTTCTTTTTCCTGAATTTTGGAATATTGCGTTACCAGTGCAT 3660
     GGATTTATTAGGGATAAAGAAGAAAAAGGACTTAAAACCTTATAACGCAATGGTCACGTA
                                                Hph I   Pst I
3661 CCGATTTCAGGTGCGGAACTCTCTGTATGGTGACTGAGGGGCCTGGAT 3708
     GGCTAAAGTCCACGCCTTGAGAGACATACCACTGACTCCCCGGACCTA
```

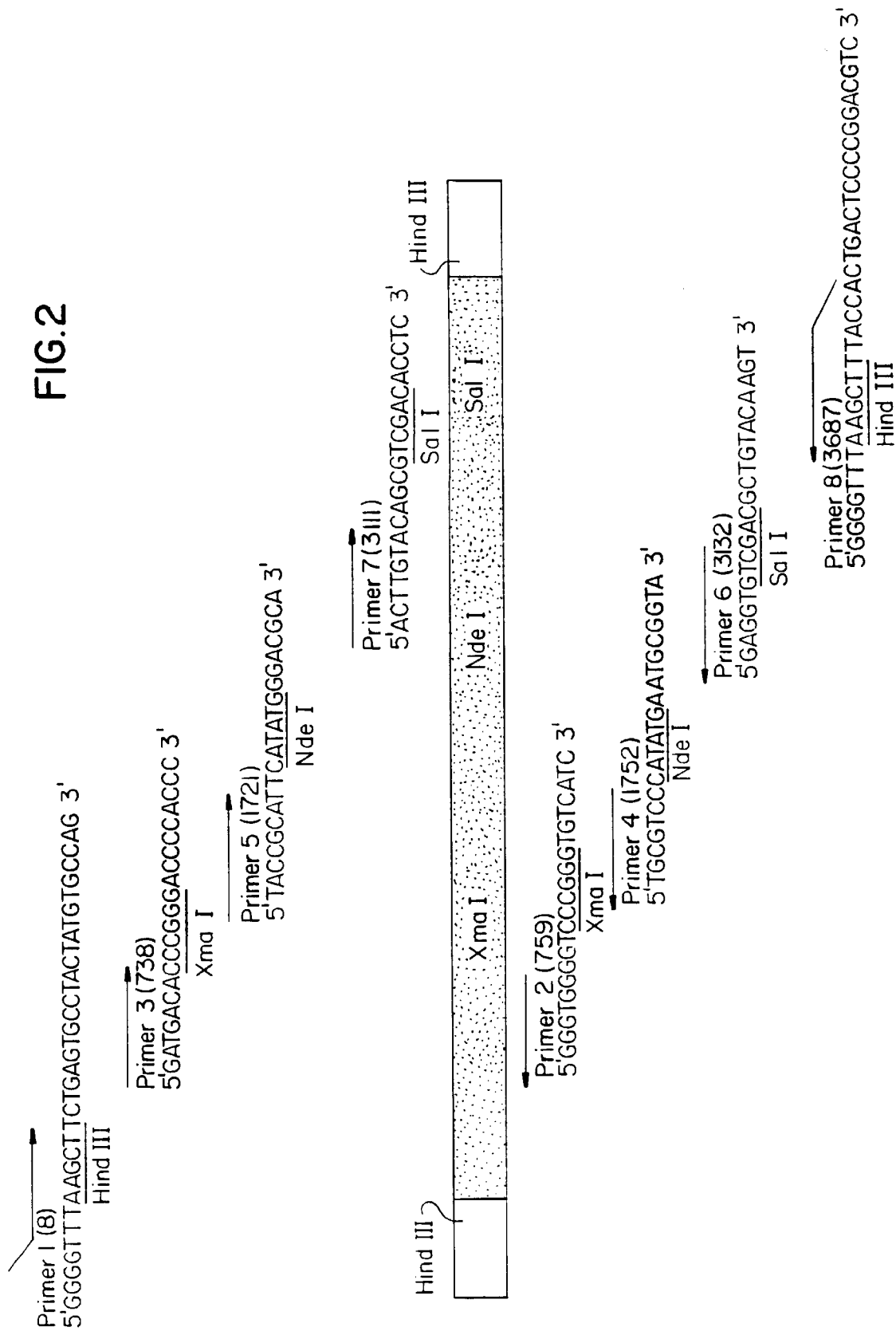

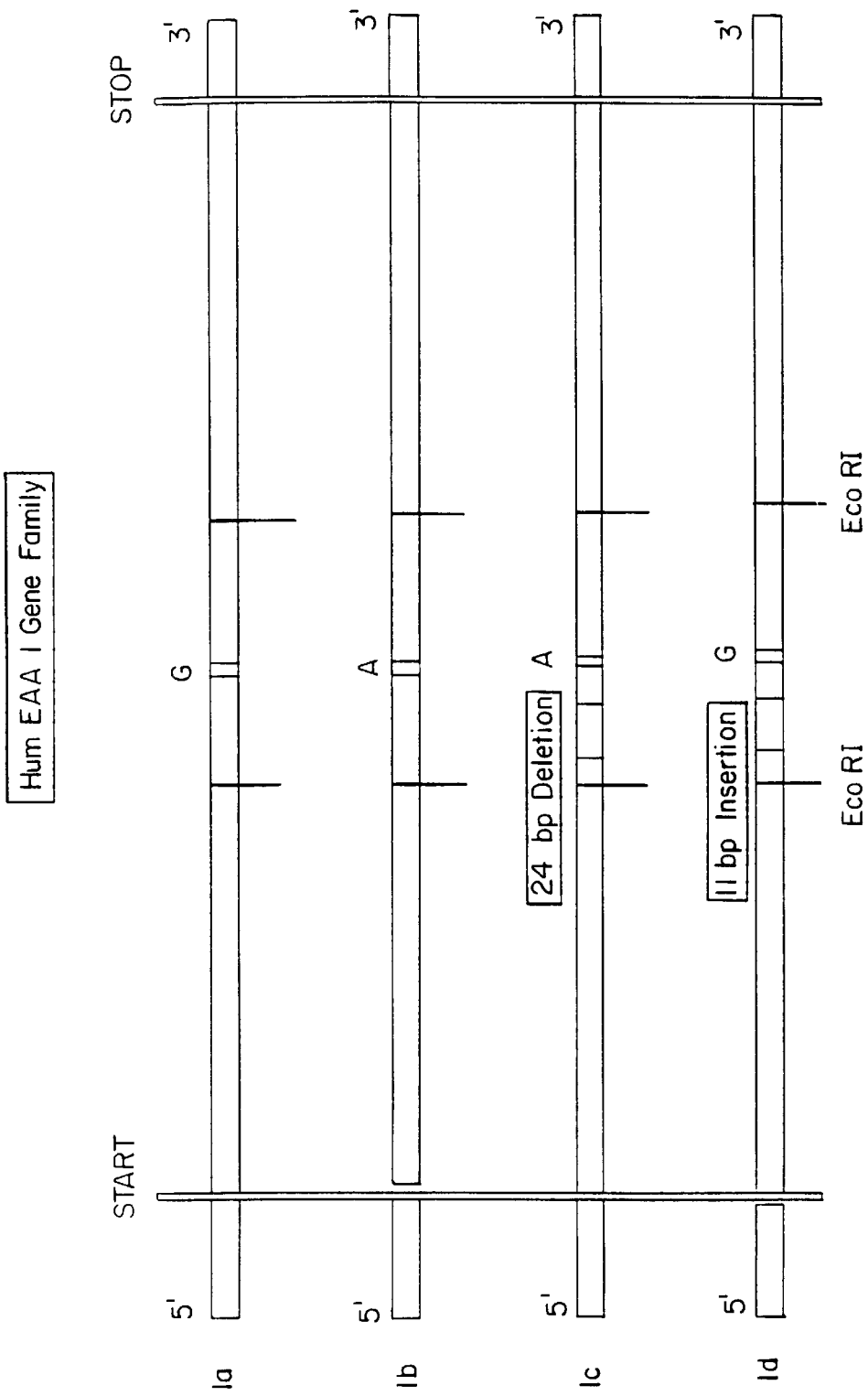

FIG. 4(b)

COMPARISON OF SELECTED REGIONS OF HUMAN EAA1 FAMILY, SHOWING SPECIFIC INSERTION (i.e. HumEAA1d), DELETION (i.e. HumEAA1c) AND NUCLEOTIDE SUBSTITUTION (i.e. HumEAA1b) RELATIVE TO HumEAA1a

```
                                    GTTTGCTGCA                                          1748
                                                                                        v
HUMAN EAA 1d    CGTCACCACCATCCT >< GGAAAACCCATATTTAATGCTGAAGGGGAACCAC ------//------ GTT---
                                                                                        Val 1737
                                                                                        v
HUMAN EAA 1a    CGTCACCACCATCCT  >< GGAA AACCCATATTTAATGCTGAAGGGGAACCAC ------//------ GTT---
Nucleotide      ^                                                                       Val
                1412

1737
                                                                                        v
HUMAN EAA 1b    CGTCACCACCATCCT >< GGAAAACCCATATTTAATGCTGAAGGGGAACCAC ------//------ ATT---
                                                                                        Ile 1713
                                                                                        v
HUMAN EAA 1c    CGTCACCACCATCCT ><..................................GGGGAACCAC ------//------ ATT---
                                                                                        Ile
```

KAINATE-BINDING HUMAN CNS RECEPTORS OF THE EAA1 FAMILY

This application is a division, of application Ser. No. 08/416,523, filed Apr. 3, 1995 U.S. Pat. No. 5,616,481, which is a continuation of Ser. No. 08/091,441, filed Jul. 15, 1993, now abandoned, which is a division of Ser. No. 08/185,232, filed Jan. 24, 1994, U.S. Pat. No. 5,576,205, which is a continuation of Ser. No. 07/750,090, filed Aug. 26, 1991 now abandoned.

FIELD OF THE INVENTION

This invention is concerned with applications of recombinant DNA technology in the field of neurobiology. More particularly, the invention relates to the cloning and expression of DNA coding for excitatory amino acid (EAA) receptors, especially human EAA receptors.

BACKGROUND TO THE INVENTION

In the mammalian central nervous system (CNS), the transmission of nerve impluses is controlled by the interaction between a neurotransmitter substance released by the "sending" neuron and a surface receptor on the "receiving" neuron. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, and various synthetic EAA receptor agonists, knowledge of EAA receptor pharmacology has been refined somewhat. Members of the EAA receptor family are now grouped into three main types based on differential binding to such agonists. One type of EAA receptor, which in addition to glutamate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (alpha-amino-3-hydroxy-5-methyl-isoxazole-4-propionate), and kainate. Particularly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

This family of glutamate-binding EAA receptors is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. However, the development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor genes, a substrate which is homogeneous for the desired receptor is provided, for drug screening programs.

Very recently, genes encoding substituent polypeptides of EAA receptors from non-human sources, principally rat, have been discovered. Hollmann et al., Nature 342: 643, 1989 described the isolation from rat of a gene referred to originally as GluR-K1 (but now called simply GluR1). This gene encodes a member of the rat EAA receptor family, and was originally suspected as being of the kainate type. Subsequent studies by Keinanen et al., Science 249: 556, 1990, showed, again in rat, that a gene called GluR-A, which was in fact identical to the previously isolated GluR1, in fact encodes a receptor not of the kainate type, but rather of the AMPA type. These two groups of researchers have since reported as many as five related genes isolated from rat sources. Boulter et al., Science 249: 1033, 1990, revealed that, in addition to GluR1, the rat contained 3 other related genes, which they called GluR2, GluR3, and GluR4, and Bettler et al., Neuron 5: 583. 1990 described GluR5. Keinanen et al., supra, described genes called GluR-A, GluR-B, GluR-C and GluR-D which correspond precisely to GluR1, GluR2, GluR3 and GluR4 respectively. Sommer et al., Science 249: 1580, 1990 also showed, for GluR-A, GluR-B, GluR-C and GluR-D two alternatively spliced forms for each gene. These authors, as well as Monyer et al., Neuron 6: 799, 1991 were able to show that the differently spliced versions of these genes were differentially expressed in the rat brain. In addition to the isolation of these AMPA receptor genes, several studies have more recently attempted to determine the ion-gating properties of different mixtures of the known receptors (Nakanishi et al., Neuron 5: 569, 1990; Hollmann et al., Science 252: 851, 1991; Verdoorn et al., Science 252: 1715, 1991; and see WO 91/06648).

Some recent work has also been published regarding non-human genes which appear to encode the kainate-type of receptor. Egebjerg et al., Nature 351: 745, 1991, have described the isolation of a gene from rat called GluR6, which although related in sequence to the AMPA receptor genes, forms a receptor which is not activated by AMPA but rather by glutamate, quisqualate, and preferentially, kainate. Other kainate-binding proteins have been described from frog (Wada et al., Nature 342: 684, 1989), chicken (Gregor et al., Nature 342: 689, 1989) and from rat (Werner et al., Nature 351: 742, 1991). These latter genes encode proteins which bind kainate, but which do not readily form into functional ion channels when expressed by themselves.

There has emerged from these molecular cloning advances a better understanding of the structural features of EAA receptors and their subunits, as they exist in the rat brain. According to the current model of EAA receptor structure, each is heteromeric in structure, consisting of individual membrane-anchored subunits, each having four transmembrane regions, and extracellular domains that dictate ligand binding properties to some extent and contribute to the ion-gating function served by the receptor complex. Keinanen et al, supra, have shown for example that each subunit of the rat GluR receptor, including those designated GluR-A, GluR-B, GluR-C and GluR-D, display cation channel activity gated by glutamate, by AMPA and by kainate, in their unitary state. When expressed in combination however, for example GluR-A in combination with GluR-B, gated ion channels with notably larger currents are produced by the host mammalian cells.

In the search for therapeutics useful to treat CNS disorders in humans, it is highly desirable of course to provide a screen for candidate compounds that is more representative of the human situation than is possible with the rat receptors isolated to date. It is particularly desirable to provide cloned genes coding for human receptors, and cell lines expressing those genes, in order to generate a proper screen for human therapeutic compounds. These, accordingly, are objects of the present invention.

It is another object of the present invention to provide in isolated form a DNA molecule which codes for a human EAA receptor.

It is another object of the present invention to provide a cell that has been genetically engineered to produce a kainate-binding human EAA receptor.

Other objects of the present invention will be apparent from the following description of the invention.

SUMMARY OF THE INVENTION

Genes coding for a family of EAA receptors endogenous to human brain have now been identified and characterized. A representative member of this human EAA receptor family, designated human EAA1a, codes for a receptor protein that in addition to binding glutamate with an affinity typical of EAA receptors, also exhibits ligand binding properties characteristic of kainate-type EAA receptors. Sequence-related genes coding for naturally occurring variants of the human EAA1a receptor have also been identified, and constitute additional members of this receptor family, herein referred to as the human EAA1 receptor family.

The present invention thus provides, in one of its aspects, an isolated polynucleotide, consisting either of DNA or of RNA, which codes for a human EAA1 receptor or for a kainate-binding fragment thereof.

In another aspect of the present invention, there is provided a cell that has been genetically engineered to produce a kainate-binding, human EAA receptor belonging to the herein-defined EAA1 family. In related aspects of the present invention, there are provided recombinant DNA constructs and relevant methods useful to create such cells.

In another aspect of the present invention, there is provided a method for evaluating the the affinity of a selected compound for binding to a receptor having the characteristics of a human EAA1 receptor, which comprises the steps of incubating the compound with a genetically engineered cell of the present invention, or with a membrane preparation derived therefrom, in a manner suitable to determine the receptor binding affinity of the test compound.

Other aspects of the present invention, which encompass various applications of the discoveries herein described, will become apparent from the following detailed description, and from the accompanying drawings.

BRIEF REFERENCE TO THE DRAWINGS

FIGS. 1a–1g provides the nucleotide sequence (SEQ ID NO: 1) of DNA coding for an excitatory amino acid receptor of the present invention, and the deduced amino acid sequence (SEQ ID NO:2) thereof;

FIG. 2 illustrates schematically a PCR-based strategy for amplifying the DNA sequence illustrated in FIG. 1 (primers 1–8 are shown in SEQ ID NOS. 3–10, respectively);

FIGS. 4a and 4b (SEQ ID NOS. 13–15) show, with reference to FIG. 1, the DNA and amino acid sequences of naturally occurring variants of the EAA receptor illustrated in FIG. 1.

DETAILED DESCRIPTION OF THE INVENTION AND ITS PREFERRED EMBODIMENTS

Figure 3A:
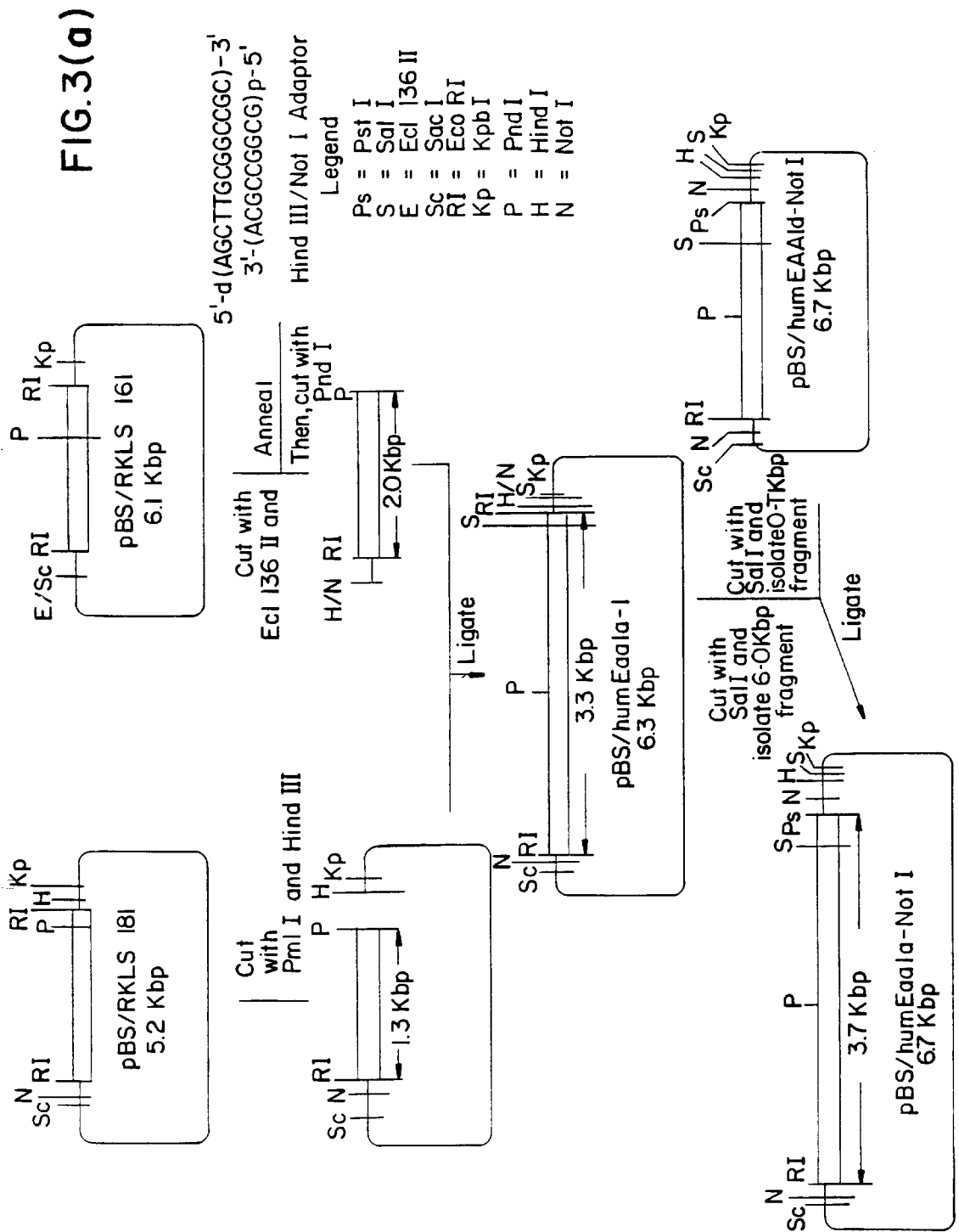
FIGS. 3a–3c illustrate with linear plasmid maps the strategy used to construct expression vectors harbouring the DNA sequence illustrated in FIG. 1 (the sequences shown in FIG. 3(1) are also disclosed in SEQ ID NOS. 11 and 12)

The invention relates to excitatory amino acid (EAA) receptors of human origin, and is directed more particularly to a novel family of kainate-type human EAA receptors, herein designated the human EAA1 receptor family. As used herein, the term "human EAA1 receptor" is intended to embrace the human EAA1a receptor, and kainate-binding variants of the EAA1a receptor that are structurally related thereto, i.e., have at least 95% homology therewith, including naturally occurring and synthetically derived variants of the EAA1a receptor. Naturally occurring variants of the human EAA1a receptor include particularly the receptors herein designated human EAA1b receptor, human EAA1c receptor and human EAA1d receptor. As used herein, the term "kainate-binding" refers to receptor variants and receptor fragments that display greater binding affinity for kainate than for either glutamate, AMPA or NMDA, as determined in assays of conventional design, such as the assays herein described.

Each of the naturally occurring members of the EAA1 family possesses structural features characteristic of the EAA receptors in general, including extracellular N- and C-terminal regions, as well as four internal hydrophobic domains which serve to anchor the receptor within the cell surface membrane. The particular human EAA receptor designated EAA1a is a protein characterized structurally as a single polypeptide chain that is produced initially in precursor form bearing an 20 residue N-terminal signal peptide, and is transported to the cell surface in mature form, lacking the signal peptide and consisting of 936 amino acids arranged in the sequence illustrated, by single letter code, in FIG. 1 (SEQ ID NOS. 1 and 2). Unless otherwise stated, amino acid residues of the EAA1 receptors are numbered with reference to the mature protein sequence. With respect to structural domains of the receptor, hydropathy analysis reveals four putative transmembrane domains, one spanning residues 527–546 inclusive (TM-1), another spanning residues 571–589 (TM-2), a third spanning residues 600–618 (TM-3) and the fourth spanning residues 785–805 (TM-4). Based on this assignment, it is likely that the human EAA1a receptor structure, in its natural membrane-bound form, consists of a 526 amino acid N-terminal extracellular domain, followed by a hydrophobic region containing four transmembrane domains and an extracellular, 131 amino acid C-terminal domain.

As shown in FIG. 4, structurally related variants of the EAA1a (shown partially in SEQ ID NO:14) receptor, which occur naturally in human brain tissue, have also been identified. As deduced from nucleotide sequences of the genes coding for them, these variants share at least about 98% amino acid homology with EAA1a, i.e., have at least about 98% identity at the amino acid level, with respect to EAA1a. One variant, designated EAA1b (shown partially in SEQ ID NO:14), is virtually identical to EAA1a except for a single nucleotide difference, which results in a GTT to ATT codon substitution, and a valine to isoleucine change at the amino acid level. The two other variants, designated EAA1c (shown partially in SEQ ID NO:15) and EAA1d (shown partially in SEQ ID NO:13), incorporate more substantial variations relative to EAA1a. The variant EAA1c is characterized by a 24 base pair deletion which results, at the amino acid level, in an eight residue deletion from an extracellular domain of the EAA1a receptor. The variant EAA1d, on the other hand, is characterized by an 11 nucleotide insertion at precisely the location where the 24 nucleotide deletion occurs in EAA1c. The 11 base pair insertion contained in EAA1d has the effect of shifting the reading frame, and in fact introduces stop codons at a location 3' of and neighbouring the insertion. As a result, the EAA1d-encoding DNA in fact encodes a truncated protein or, in essence, an extracellular fragment of EAA1a.

In human hippocampal cDNA libraries, the source from which DNA coding for the EAA1a receptor was isolated, the EAA1a receptor is encoded by the nucleotide sequence provided in FIG. 1 (SEQ ID NOS. 1 and 2). Relative to EAA receptors previously discovered in rat tissue, as described in the publications mentioned hereinabove, members of the human EAA1 receptor family share not more than about 45% amino acid identity with such rat receptors, with the exception of the rat KA-1 protein described very recently by Werner et al, 1991, supra, which shares about 94% amino acid homology (identity) with human EAA1a. The human EAA1 receptors differ most significantly from this rat receptor in the extracellular, C-terminal region of the receptors.

Like other members of the human EAA1 receptor family, receptor subtype EAA1a is characterized by a pharmacological profile i.e. a ligand binding "signature", that points strongly to a kainate-type pharmacology, as distinct from other excitatory amino acid receptor types, such as NMDA and AMPA. Despite the understanding that kainate binding receptors require a multi- and perhaps heteromeric subunit structure to function in the pharmacological sense, it has been found that cells producing the unitary EAA1a receptor do, independently of association with other receptor subunits, provide a reliable indication of excitatory amino acid binding. Thus, in a key aspect of the present invention, the human EAA1a receptor is exploited for the purpose of screening candidate compounds for the ability to compete with endogenous EAA receptor ligands and known synthetic analogues thereof, for EAA receptor binding.

For use in receptor binding assays, it is desirable to construct by application of genetic engineering techniques a mammalian cell that produces a human EAA1 receptor in functional form as a heterologous product. The construction of such cell lines is achieved by introducing into a selected host cell a recombinant DNA construct in which DNA coding for the human EAA1 receptor in a form transportable to the cell surface i.e., bearing its native signal peptide or a functional, heterologous equivalent thereof, is associated with expression controlling elements that are functional in the selected host to drive expression of the receptor-encoding DNA, and thus elaborate the desired EAA1 receptor protein. Such cells are herein characterized as having the receptor-encoding DNA incorporated "expressibly" therein. The receptor-encoding DNA is referred to as "heterologous" with respect to the particular cellular host if such DNA is not naturally found in the particular host. The particular cell type selected to serve as host for production of the human EAA1 receptor can be any of several cell types currently available in the art, but should not of course be a cell type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human-type cells may nevetheless serve as expression hosts, provided that "background" binding to the test ligand is accounted for in the assay results.

According to one embodiment of the present invention, the cell line selected to serve as host for EAA1 receptor production is a mammalian cell. Several types of such cell lines are currently available for genetic engineering work, and these include the chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L--cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available, and any one of these systems can be selected to drive expression of the EAA1 receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which DNA coding for the transportable receptor precursor is linked with expression controlling DNA sequences recognized by the host, and which include a region 5' of the receptor-encoding DNA to drive expression, and a 3' region to terminate expression. The plasmidic vector harbouring the expression construct typically incorporates such other functional components as an origin of replication, usually virally-derived, to permit replication of the plasmid in the expression host and desirably also for plasmid amplification in a bacterial host, such as *E.coli*. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heavy metals, i.e., the metalothionein gene promoter, and other steroid-inducible promoters.

For incorporation into the recombinant DNA expression vector, DNA coding for the desired EAA1 receptor, i.e., the EAA1a receptor or a kainate-binding variant thereof, can be obtained by applying selected techniques of gene isolation or gene synthesis. As described in more detail in the examples herein, the EAA1a receptor, and the EAA1b, EAA1c and EAA1d variants thereof, are encoded within the genome of human brain tissue, and can therefore be obtained by careful application of conventional gene isolation and cloning techniques. This typically will entail extraction of total messenger RNA from a fresh source of human brain tissue, preferably cerebellum or hippocampus tissue, followed by conversion of message to cDNA and formation of a library in for example a bacterial plasmid, more typically a bacteriophage. Such bacteriophage harbouring fragments of the human DNA are typically grown by plating on a lawn of susceptible *E. coli* bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled oligonucleotide probe of appropriate sequence to identify the particular phage colony carrying receptor-encoding DNA or fragment thereof. Typically, the gene or a portion thereof so identified is subcloned into a plasmidic vector for nucleic acid sequence analysis.

Having herein provided the nucleotide sequence of various human EAA1 receptors, it will be appreciated that automated techniques of gene synthesis and/or amplification can be performed to generate DNA coding therefor. Because of the length of the EAA1 receptor-encoding DNA, application of automated synthesis may require staged gene construction, in which regions of the gene up to about 300 nucleotides in length are synthesized individually and then ligated in correct succession for final assembly. Individually synthesized gene regions can be amplified prior to assembly, using polymerase chain reaction (PCR) technology.

The application of automated gene synthesis techniques provides an opportunity for generating sequence variants of naturally occurring members of the EAA1 gene family. It will be appreciated, for example, that polynucleotides coding for the EAA1 receptors herein described can be generated by substituting synonymous codons for those represented in the naturally occurring polynucleotide sequences herein identified. In addition, polynucleotides coding for synthetic variants of the EAA1 receptors herein described can be generated which for example incorporate one or more single amino acid substitutions, deletions or additions. Since it will for the most part be desirable to retain the natural ligand binding profile of the receptor for screening purposes, it is desirable to limit amino acid substitutions, for example to the so-called conservative replacements in which amino acids of like charge are substituted, and to limit substitutions to those sites less critical for receptor activity, e.g., within about the first 20 N-terminal residues of the mature receptor, and such other regions as are elucidated upon receptor domain mapping.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector, and host cells are transfected therewith using conventional procedures, such as DNA-mediated transformation, electroporation, or particle gun transformation. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers include the *E. coli* gpt gene which confers resistance to mycophenolic acid, the neo gene from transposon Tn5 which confers resistance to the antibiotic G418 and to neomycin, the dhfr sequence from murine cells or *E. coli* which changes the phenotype of DHFR−cells into DHFR+cells, and the tk gene of herpes simplex virus, which makes TK−cells phenotypically TK+cells. Both transient expression and stable expression can provide transformed cell lines, and membrane preparations derived therefrom, for use in ligand screening assays.

For use in screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e., ligand binding experiments, frozen intact cells are homogenized while in cold water suspension and a membrane pellet is collected after centrifugation. The pellet is then washed in cold water, and dialyzed to remove endogenous EAA ligands such as glutamate, that would otherwise compete for binding in the assays. The dialyzed membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The binding of a candidate ligand to a selected human EAA1 receptor of the invention is evaluated typically using a predetermined amount of cell-derived membrane (measured for example by protein determination), generally from about 25 $\mu$g to 100 $\mu$g. Generally, competitive binding assays will be useful to evaluate the affinity of a test compound relative to kainate. This competitive binding assay can be performed by incubating the membrane preparation with radiolabelled kainate, for example [$_3$H]-kainate, in the presence of unlabelled test compound added at varying concentrations. Following incubation, either displaced or bound radiolabelled kainate can be recovered and measured, to determine the relative binding affinities of the test compound and kainate for the particular receptor used as substrate. In this way, the affinities of various compounds for the kainate-type human EAA receptors can be measured.

As an alternative to using cells, that express receptor-encoding DNA, ligand characterization may also be performed using cells for example Xenopus oocytes, that yield functional membrane-bound receptor following introduction of messenger RNA coding for the EAA1 receptor. In this case, the EAA1 receptor gene of the invention is typically subcloned into a plasmidic vector such that the introduced gene may be easily transcribed into RNA via an adjacent RNA transcription promoter supplied by the plasmidic vector, for example the T3 or T7 bacteriophage promoters. RNA is then transcribed from the inserted gene in vitro, and can then be injected into Xenopus oocytes. Following the injection of nL volumes of an RNA solution, the oocytes are left to incubate for up to several days, and are then tested for the ability to respond to a particular ligand molecule supplied in a bathing solution. Since functional EAA receptors act in part by operating a membrane channel through which ions may selectively pass, the functioning of the receptor in response to a particular ligand molecule in the bathing solution may typically be measured as an electrical current utilizing microelectrodes inserted into the cell.

In addition to using the receptor-encoding DNA to construct cell lines useful for ligand screening, expression of the DNA can, according to another aspect of the invention, be performed to produce fragments of the receptor in soluble form, for structure investigation, to raise antibodies and for other experimental uses. It is expected that the portion of the EAA1 receptor responsible for binding a ligand molecule resides of the outside of the cell, i.e., is extracellular. It is therefore desirable in the first instance to facilitate the characterization of the receptor-ligand interaction by providing this extracellular ligand-binding domain in quantity and in isolated form, i.e., free from the remainder of the receptor. To accomplish this, the full-length EAA1 receptor-encoding DNA may be modified by site-directed mutagenesis, so as to introduce a translational stop codon into the extracellular N-terminal region, immediately before the sequence encoding the first transmembrane domain (TM1), i.e., before residue 527 as shown in FIG. 1 (SEQ ID NOS. 1 and 2). Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

Alternatively, it may be desirable to produce an extracellular domain of the receptor which is not derived from the amino-terminus of the mature protein, but rather from the carboxy-terminus instead, for example domains immediately following the fourth transmembrane domain (TM4), i.e., residing between amino acid residues 805 and 936 inclusive of FIG. 1. In this case, site-directed mutagenesis and/or PCR-based amplification techniques may readily be used to provide a defined fragment of the gene encoding the receptor domain of interest. Such a DNA sequence may be used to direct the expression of the desired receptor fragment, either intracellularly, or in secreted fashion, provided that the DNA encoding the gene fragment is inserted adjacent to a translation start codon provided by the expression vector, and that the required translation reading frame is carefully conserved.

It will be appreciated that the production of such extracellular ligand binding domains may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf9 (Spodoptera frugiperda) cells may be used, with the expression typically being driven by expression promoters of the baculovirus, for example the strong, late polyhedrin protein promoter. Filamentous fungal expression systems may also be used to secrete large quantities of such extracellular domains of the EAA receptor. Aspergillus nidulans, for example, with the expression being driven by the alcA promoter, would constitute such an acceptable system. In addition to such expression hosts, it will be further appreciated that any prokaryotic or other eukaryotic expression system capable of expressing heterologous genes or gene fragments, whether intracellularly or extracellularly would be similarly acceptable.

The availability of isolated extracellular ligand-binding domains of the receptor protein makes it feasible to determine the 3-dimensional structures of these ligand-binding regions, with or without a candidate ligand complexed thereto, by a combination of X-ray crystallographic and advanced 2D-NMR techniques. In this way, additional new candidate compounds, predicted to have the required interactions with the 3-dimensional receptor structure, can be specifically designed and tested.

With large domains, crystallography is the method of choice for structure determination of both the domain in isolation, and of the co-complex with the natural ligand (or an appropriate antagonist or agonist molecule). If a particular domain can be made small enough, for example approximately 100–130 amino acids in length, then the powerful technique of 2-D NMR can also be applied to structure determination. This enables not only the determination of the domain structure, but also provides dynamic information about the drug-receptor interaction.

For use particularly in detecting the presence and/or location of an EAA1 receptor, for example in brain tissue, the present invention also provides, in another of its aspects, labelled antibody to a human EAA1 receptor. To raise such antibodies, there may be used as immunogen either the intact, soluble receptor or an immunogenic fragment thereof, produced in a microbial or mammalian cell host as described above or by standard peptide synthesis techniques. Regions of the EAA1a receptor particularly suitable for use as immunogenic fragments include those corresponding in sequence to an extracellular region of the receptor, or a portion of the extracellular region, such as peptides consisting of residues 1–526, including particularly residues 106–120 or 178–191 or 463–509, and peptides corresponding to the region between transmembrane domains TM-2 and TM-3, such as a peptide consisting of residues 590–599. Peptides consisting of the C-terminal domain (residues 806–936), or fragment thereof such as a peptide consisting of residues 895–936 or 915–930, may also be used for the raising of antibodies. Substantially the same regions of the human EAA1b, EAA1c and EAA1d receptors may also be used for production of antibodies against these receptors.

The raising of antibodies to the desired EAA1 receptor or immunogenic fragment can be achieved, for polyclonal antibody production, using immunization protocols of conventional design, and any of a variety of mammalian hosts, such as sheep, goats and rabbits. Alternatively, for monoclonal antibody production, immunocytes such as splenocytes can be recovered from the immunized animal and fused, using hybridoma technology, to a myeloma cells. The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using linker technology established for this purpose.

In detectably labelled form, e.g. radiolabelled form, DNA or RNA coding for the human EAA1 receptor, and selected regions thereof, may also be used, in accordance with another aspect of the present invention, as hybridization probes, for example to identify sequence-related genes resident in the human or other mammalian genomes (or cDNA libraries) or to locate the EAA1 -encoding DNA in a specimen, such as brain tissue. This can be done using either the intact coding region, or a fragment thereof having radiolabelled, e.g. $^{32}$P, nucleotides incorporated therein. To identify the EAA1-encoding DNA in a specimen, it is desirable to use either the full length cDNA coding therefor, or a fragment which is unique thereto. With reference to FIG. 1 and the nucleotide numbering appearing thereon, such nucleotide fragments include those corresponding in sequence to a region coding for the N-terminus or C-terminus of the receptor, or representing a 5'-untranslated or 3'-untranslated region thereof, such as one of the following nucleotide regions: 8–156, 157–1563, 531–575, 1278–1359, 2826–2909, 2958–3073 and 3024–3708. These sequences, and the intact gene itself, may also be used of course to clone EAA1-related human genes, particularly cDNA equivalents thereof, by standard hybridization techniques.

EXAMPLE 1

Isolation of DNA coding for the human EAA1a receptor

As a first step in the isolation of DNA coding for a human EAA receptor, the published nucleotide sequences of rat GluR1 receptor, and chicken and frog kainate binding proteins were compared to identify spaced regions of homology, capable of serving as sites for primer binding, and PCR-based amplification. Oligonucleotide primers putatively capable of hybridizing with sequence-related regions in human cDNA, and having non-hybridizing flanks bearing HindIII restriction sites for subsequent cloning work, were then synthesized based on the published sequence of the rat GluR1 gene using conventional techniques of gene synthesis, to generate primers of the following sequence:

(SEQ ID NO: 16) 5' GGGGTTTAAGCT-TGAGCGTCGTCCTCTTCCTGGT 3'

(SEQ ID NO: 17) 5' GGGGTTTAAGCTTGTAA-GAACCACCAGACGCCG 3'

Using human hippocampal CDNA as template (obtained as an EcoRI-based lambda gt10 library from Clontech Laboratories (Palo Alto, Calif., U.S.A.) the primers were then used in an attempt to amplify homologous sequences in the human CDNA, by application of the polymerase chain reaction technique. Reaction mixtures contained, in 100 μl, 100 ng of human hippocampal cDNA, 125 pmol of each primer and 2 U Taq polymerase (in 10 mM Tris-HCl, pH9.0, 50 mM KCl, 1.5 mM MgCl$_2$, and with 0.2 mM of each deoxyribonucleotide species). There were then performed thirty cycles of 94 C./1 min; 58 C./1 min; 72 C./2 min, followed by a final cycle of 72 C./30 min.

There was generated an amplification product having an expected nucleotide length (239 bp). The product of amplification was then liberated from the gel and sub-cloned for sequencing into the HindIII site of phagemid vector pTZ19 (Pharmacia). The nucleotide sequence of the amplification product (without primers) is represented, retrospectively, from nucleotide #1850 to nucleotide #2020 inclusive (FIG. 1, SEQ ID NOS 1 and 2). A comparison of the sequence amplified from the human CDNA template with the corresponding region of the rat GluR gene on which the oligonucleotide primers were based revealed only about 60% identity, indicating that a fragment from an unrelated human gene had been identified.

To isolate cDNA coding for the entire human EAA1a receptor, a lambda gt10-based library of human hippocampal cDNA was probed using a PCR-generated, labelled (alpha-$^{32}$P-dCTP) version of the 239 bp amplification product. Of 10$^6$ clones screened, probing identified 60 putative clones under the following high stringency hybridization conditions: 6×SSC, 50% formamide, 5% Denhardt's solution, 0.5% SDS, 100 μg/ml denatured salmon sperm DNA. Hybridizations were carried out at 37 C. overnight, and filters were washed with 2×SSC containing 0.5% SDS at 25 C. for 5 minutes, followed by a 15 minute wash at 50 C. with 2×SSC containing 0.5% SDS. The final wash was with 1×SSC containing 0.5% SDS at 50 C. for 15 minutes. Filters were exposed to X-ray film (Kodak) overnight.

Hybridization studies were performed in duplicate, and only those clones which hybridized well in both duplicates were selected for further analysis. Upon second round screening, 50 of the original 60 putative clones were selected. All 50 putative clones were plaque-purified, large scale DNA preps were made, and then DNA inserts liberated therefrom were subcloned into the EcoRI site of pTZ18 vectors, for sequence analysis. Sequencing revealed one clone harbouring, internally, a region with a nucleotide sequence identical to the sequence of the original 239 bp subclone. The entire sequence of the isolated clone (1058 bp) was then determined. Retrospectively, this 1058 bp sub-clone is represented from nucleotide 1245 to nucleotide 2302 inclusive (FIG. 1, SEQ ID NOS 1 and 2).

Figure 3B:
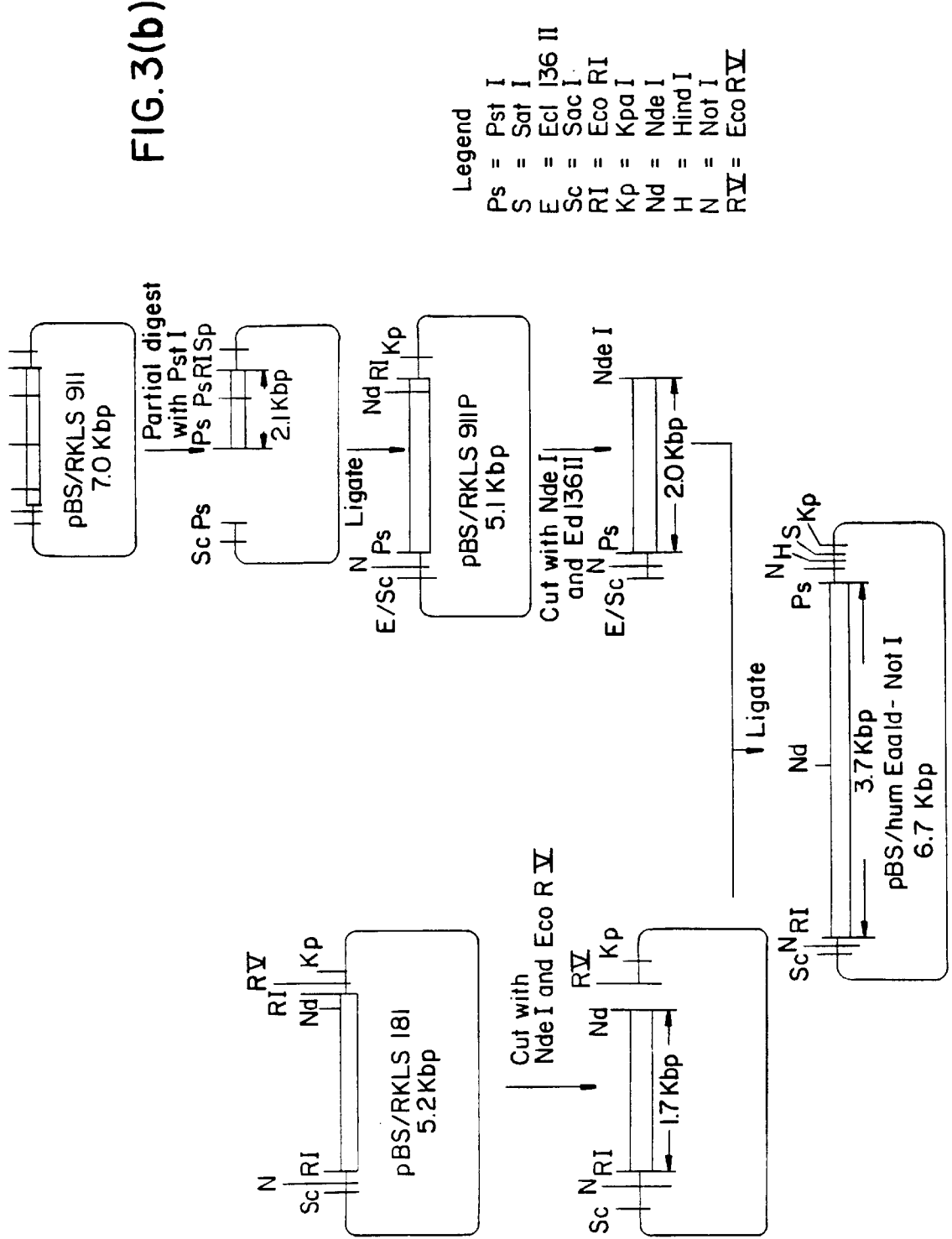
Figure 3C:
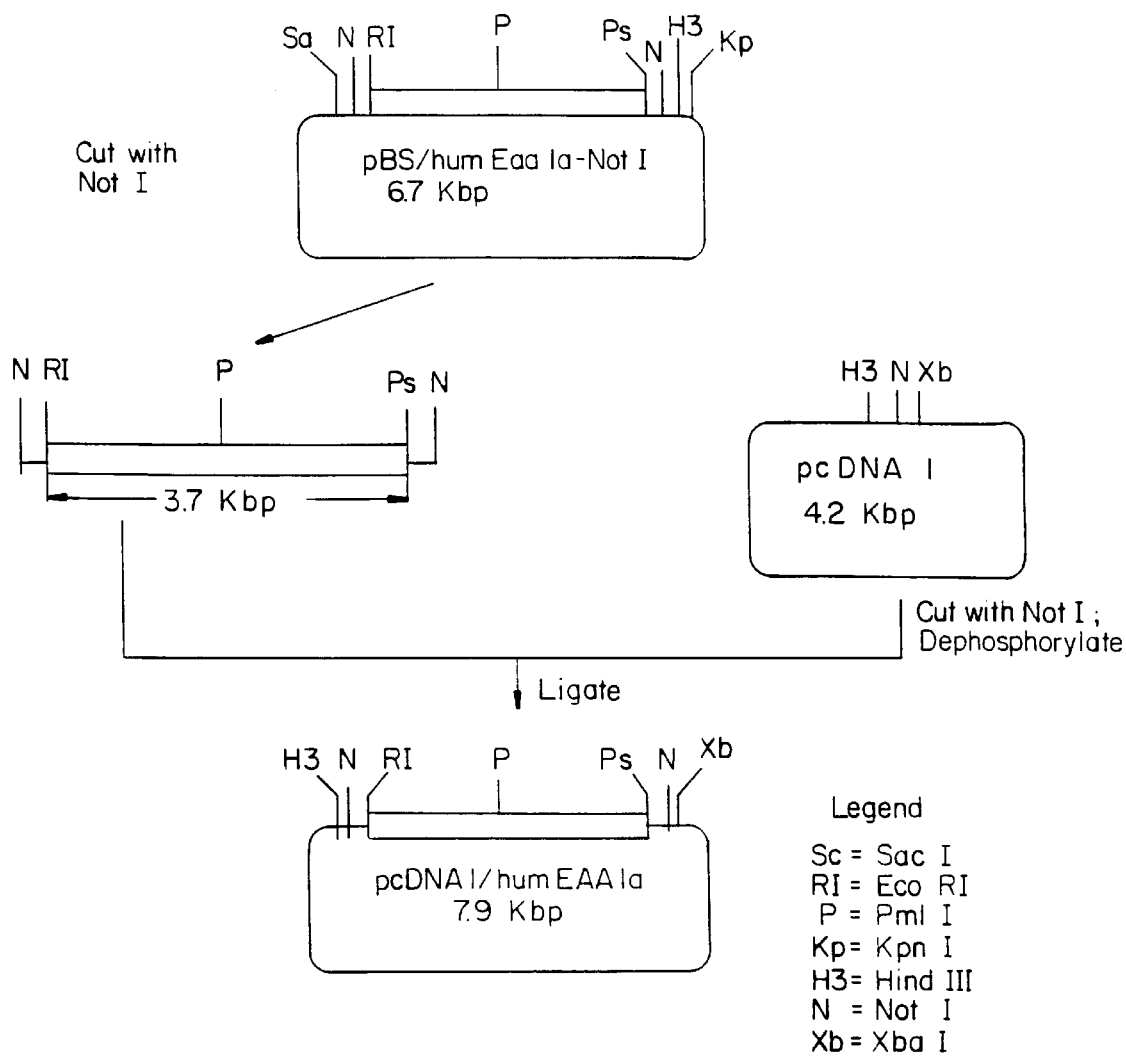

Since it was likely by analogy with the other receptor genes that the 1058 bp was not full length, an alternative human hippocampal cDNA library constructed in a lambda phage system known commercially as lambda ZAP II was obtained (Stratagene Cloning Systems, La Jolla, Calif., U.S.A.) and screened using a PCR-generated, radiolabelled version of the 1058 bp sub-clone. Screening of 10$^6$ clones of this library by hybridization under the stringency conditions detailed above lead initially to the selection of 50 positive clones. For sequencing, phagemids carrying the inserts were excised, to generate insert-carrying variants of the phagemid vector known commercially as Bluescript-SK. Sequencing analysis identified two phagemid clones sharing a sequence overlap. One clone carrying a 2.2 kb EcoRI/EcoRI insert, and apparently representing a 5' region of the open reading frame, was designated pBS/RKLS181. The overlapping clone carrying a 3.1 kb EcoRI/EcoRI insert and appearing to represent the remaining 3' region of the open reading frame, was designated pBS/RKLS161. To construct the entire open reading frame, the strategy shown in FIG. 3(1) was employed, to generate the phagemid pBS/HumEAA1a which carries the EAA1a-encoding DNA as a 3.7 kb EcoRI/PstI insert (recoverable intact as a 3.7 kb NotI/NotI insert) in a 3.0 kb Bluescript-SK phagemid background. The entire sequence of the EcoRI/PstI insert is provided in FIG. 1 (SEQ ID NOS 1 and 2).

The 6.7 kb phagemid pBS/humEAA1a-NotI was deposited, under the terms of the Budapest Treaty, with the American Type Culture Collection in Rockville, Md. USA on Aug. 21, 1991, and has been assigned accession number ATCC 75063.

EXAMPLE 2

Alternative strategy for obtaining EAA1a receptor-encoding DNA

Having herein provided the nucleotide sequence of EAA1a-encoding DNA, it will be appreciated that isolation thereof by the procedures just described is unnecessary, and can be replaced by application of automated techniques of gene synthesis and amplification. Using an appropriate cDNA library as template, for example a carefully prepared human hippocampal cDNA library, the polymerase chain reaction technique can be applied to amplify the desired cDNA product. While current PCR protocols are unlikely to enable direct amplification of the entire 3.7 kb gene, regional amplification to generate ligatable gene fragments is a feasible approach to gene construction.

With reference specifically to the EAA1a-encoding DNA, PCR-facilitated gene construction can proceed, for example, as illustrated in FIG. 2 (SEQ ID NOS 3–10). More particularly, regions of the cloned cDNA template are amplified as fragments comprising on the order of several hundred nucleotides, using primers bearing non-hybridizing 5' flanks that constitute restriction sites useful in subsequent steps of gene assembly. In the example illustrated in FIG. 2, the gene is amplified as 4 individual fragments that can be ligated, because of the careful selection of restriction sites, in one step to form the entire EAA1a receptor-encoding DNA.

It will also be appreciated that automated techniques of gene synthesis can be applied, to provide gene fragments that by PCR can be amplified and subsequently ligated. Using current protocols, for example as described by Barnett et al in Nucl. Acids Res., 1990, 18(10):3094, fragments up to about 300 bases in length can be synthesized, and then amplified again using restriction site-tailed primers to facilitate assembly of the de novo synthesized gene regions.

EXAMPLE 3

Construction of genetically engineered cells producing the human EAA1a receptor

For transient expression in mammalian cells, cDNA coding for the human EAA1a receptor was incorporated into the mammalian expression vector pcDNA 1, which is available commercially from Invitrogen Corporation (San Diego, Calif., USA; catalogue number V490-20). This is a multi-functional 4.2 kb plasmid vector designed for cDNA expression in eukaryotic systems, and cDNA analysis in prokaryotes. Incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

For incorporation of the EAA1a receptor-encoding cDNA into an expression vector, the cDNA source insert was released from pBS/hum EAA1a-NotI as a 3.7 kb NotI/NotI fragment, which was then incorporated at the NotI site in the pcDNAI polylinker. Sequencing across the NotI junction was performed, to confirm proper insert orientation in pcDNA1. The resulting plasmid, designated pcDNA1/humEAA1a, was then introduced for transient expression into a selected mammalian cell host, in this case the monkey-derived, fibroblast like cells of the COS-1 lineage (available from the American Type Culture Collection, Rockville, Md. as ATCC CRL 1650).

For transient expression of the EAA1-encoding DNA, COS-1 cells were transfected with approximately 8 $\mu$g DNA (as pcDNA1/humEAA1a) per $10^6$ COS cells, by DEAE-mediated DNA transfection and treated with chloroquine according to the procedures described by Maniatis et al, supra. Briefly, COS-1 cells were plated at a density of $5\times10^6$ cells/dish and then grown for 24 hours in FBS-supplemented DMEM/F12 medium. Medium was then removed and cells were washed in PBS and then in medium. There was then applied on the cells 10 ml of a transfection solution containing DEAE dextran (0.4 mg/ml), 100 $\mu$M chloroquine, 10% NuSerum, DNA (0.4 mg/ml) in DMEM/F12 medium. After incubation for 3 hours at 37 C., cells were washed in PBS and medium as just described and then shocked for 1 minute with 10% DMSO in DMEM/F12 medium. Cells were allowed to grow for 2–3 days in 10% FBS-supplemented medium, and at the end of incubation dishes were placed on ice, washed with ice cold PBS and then removed by scraping. Cells were then harvested by centrifugation at 1000 rpm for 10 minutes and the cellular pellet was frozen in liquid nitrogen, for subsequent use in ligand binding assays. Northern blot analysis of a thawed aliquot of frozen cells confirmed expression of receptor-encoding cDNA in cells under storage.

In a like manner, stably transfected cell lines were also prepared using two different cell types as host: CHO K1 and CHO Pro5. To construct these cell lines, cDNA coding for human EAA1a was incorporated into the NotI site of a 7.1 kb derivative of plasmid vector pcDNA1, which incorporates the neomycin gene under control of the Rous Sarcoma Virus LTR promoter and is designated pcDNA1/NEO (available also from Invitrogen Corporation, catalogue #V492-20). In a similar fashion, and again using a convenient NotI site for insertion, the receptor-encoding cDNA was inserted into the mammalian expression vector pRC/CMV (Invitrogen), which enables stable expression. Insertion at this site placed the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells were first seeded at a density of $5\times10^5$ in 10% FBS-supplemented MEM medium. After growth for 24 hours, fresh medium was added to the plates and three hours later, the cells were transfected using the calcium phosphate-DNA co-precipitation procedure (Maniatis et al, supra). Briefly, 3 $\mu$g of DNA was mixed and incubated with buffered calcium solution for 10 minutes at room temperature. An equal volume of buffered phosphate solution was added and the suspension was incubated for 15 minutes at room temperature.. Next, the incubated suspension was applied to the cells for 4 hours, removed and cells were shocked with medium containing 15% glycerol. Three minutes later, cells were washed with medium and incubated for 24 hours at normal growth conditions. Cells resistant to neomycin were selected in 10% FBS-supplemented alpha-MEM medium containing G418 (1 mg/ml). Individual colonies of G418-resistant cells were isolated about 2–3 weeks later, clonally selected and then propogated for assay purposes.

EXAMPLE 4

Ligand binding assays

Transfected cells in the frozen state were resuspended in ice-cold distilled water using a hand homogenizer and centrifuged for 20 minutes at 50,000 g. The supernatant was discarded and the membrane pellet stored frozen at −70° C.

COS cell membrane pellets were suspended in ice cold 50 mM Tris-HCl (pH 7.55, 5° C.) and placed inside Spectrapor 7 (EDTA-treated, sulfur-free) dialysis tubing. The suspension was placed in 4 liters of ice cold 50 mM Tris-HCl (pH 7.55, 5° C.) and dialyzed for 16–24 hours at 5° C. in order to remove endogenous glutamate that would compete for binding. The tissue suspension was recovered from the tubing along with a small volume of buffer used to rinse the tubing. This resultant membrane preparation was used as tissue source for binding experiments described below. Proteins were determined using the Pierce Reagent with BSA as standard.

Binding assays were then performed, using an amount of COS-derived membrane equivalent to from 25–100 μg as judged by protein determination and selected radiolabelled ligand. In particular, glutamate binding assays entailed formation of an incubation mixture consisting of 25–100 μg of tissue protein, and [3,4-3H]L-glutamic acid (47.3 Ci/mmole, 10 nM final) in 50 mM Tris-HCl (pH 7.55, SC) in 1 ml final volume. Non-specific binding was in the presence of 1 mM L-glutamate. Samples were incubated on ice for 60 minutes in plastic minivials. Bound and free ligand were separated by centrifugation for 10 minutes at 50,000 g (4 C.). Tissue pellets were washed superficially with 2×6 ml of ice cold incubation buffer. Pellets were solubilized and counted in 5 ml of Beckman Ready Protein Scintillation cocktail.

For kainate binding assays, incubation mixtures consisted of 25–100 μg tissue protein and [vinylidene-$^3$H] kainic acid (58 Ci/mmole, 5 nM final) in the cold incubation buffer, 1 ml final volume. Non-specific binding was in the presence of 1 mM L-glutamate. Samples were incubated as for the glutamate binding assays, and bound and free ligand were separated by rapid filtration using a Brandel cell harvester and GF/B filters pre-soaked in ice-cold 0.3% polyethyleneimine. Filters were washed twice in 6 ml of the cold incubation buffer, then placed in scintillation vials with 5 ml of Beckman Ready-Safe scintillation cocktail for counting.

AMPA-binding assays were also performed in substantially the same manner described above for kainate binding, but using as ligand D,L-alpha-[5-methyl-$^3$H]amino-3-hydroxy-5-methylisoxazole-amino-4-propionic acid (amino-3H-AMPA, amino-27.6 Ci/mmole, amino-5 nM final) with 0.1M KSCN and 2.5 mM $CaCl_2$ in the 1 ml final volume.

Figure 5:
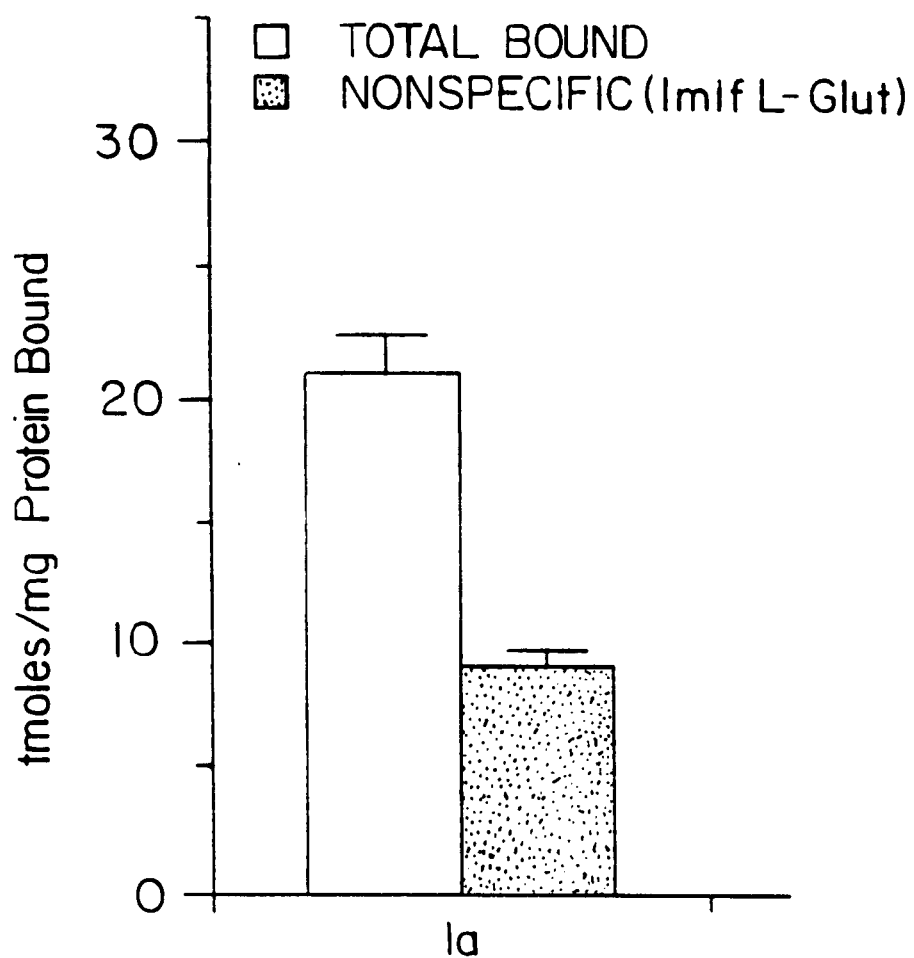
FIG. 5 illustrates graphically the ligand-binding properties of the EAA receptor expressed from the coding region provided in FIG. 1.

Assays performed in this manner, using membrane preparations derived from the EAA1a-producing COS cells, revealed specific [$^3$H]-kainate binding at 5 nM and [3H]-glutamate binding at 10 nM, labelled ligand (FIG. 5). Mock transfected cells exhibited no specific binding of any of the ligands tested. These results demonstrate clearly that the human EAA1a receptor is binding kainate with high affinity. This activity, coupled with the fact that there is little or no demonstrable binding of either AMPA or NMDA clearly assigns the EAA1a receptor to be of the kainate type of EAA receptor. Furthermore, this binding profile, especially with the kainate binding being of the high affinity category (i.e. nanomolar range) indicates that the receptor is functioning in an authentic manner, and can therefore reliably predict the ligand binding "signature" of its non-recombinant counterpart from the intact human brain. These features make the recombinant receptor especially useful for selecting and characterizing ligand compounds which bind to the receptor, and/or for selecting and characterizing compounds which may act by displacing other ligands from the receptor. The isolation of the EAA1a receptor gene in a pure form, capable of being expressed as a single, homogenous receptor species, therefore frees the ligand binding assay from the lack of precision introduced when complex, heterogeneous receptor preparations from human brains are used to attempt such characterizations.

EXAMPLE 5

Naturally occurring variants of the human EAA1a receptor

Using the same 1058 bp probe which lead to the successful identification of the human EAA1a receptor, three sequence-related variants thereof were also identified and isolated, in substantially the same manner. As shown in FIG. 4, one variant designated EAA1d (shown partially in SEQ ID NO:13) is similar in many structural respects to the human EAA1a (shown partially in SEQ ID NO:14) receptor, and differs only by the precise insertion in EAA1d of an 11 bp insertion, between nucleotide positions 1426 and 1427 of EAA1a. Like DNA coding for EAA1a, the EAA1d-encoding DNA was isolated from a cDNA library of human hippocampal DNA. To construct the full length cDNA containing the entire open reading frame, overlapping clones pBS/RKLS181 (representing the 5'-region) and pBS/RKLS911 (representing the 3'-region) were combined using the strategy shown in FIG. 3(2). For binding studies, the isolated cDNA insert has been released from pBShumEAA1d-NotI, as a 3.7 kb NotI/NotI fragment, and has been introduced for transient expression into cells of the COS-1 lineage after insertion into the vector pcDNA1 and, for stable expression, into CHO K1 or CHO Pro5 cells after insertion into vectors pcDNA1/NEO and pRC/CMV, all in the same manner as described above for human EAA1a.

A plasmid, designated pBS/humEAA1d-NotI, which carries a 3.7 kb NotI/NotI cDNA insert coding for the human EAA1d receptor in a 3.0 kb Bluescript-SK background, has been deposited, under the terms of the Budapest Treaty, with the American Type Culture Collection in Rockville, Md. USA on Aug. 21, 1991, under accession number ATCC 75064.

Another variant uncovered in the human hippocampal cDNA library using the same cloning strategy, designated the human EAA1b (shown partially in SEQ ID NO:14) receptor, is nearly identical in all respects to EAA1a, except for a single nucleotide difference at position #1737 which results in a valine to isoleucine change within the extracellular N-terminal region of EAA1a, as shown in FIG. 4. DNA coding for a third variant designated human EAA1c (shown partially in SEQ ID NO:15) was also isolated using the herein described cloning strategy and the human hippocampal cDNA library, carries a 24 bp (8 amino acid) deletion relative to EAA1a, in the extracellular N-terminal region thereof (FIG. 4).

We claim:

1. A human EAA1 receptor selected from the group consisting of
   an EAA1a receptor having the amino acid sequence of residues 1–936 of SEQ ID NO:2 with a valine residue at amino acid position 508;
   an EAA1b receptor having the amino acid sequence of residues 1–936 of SEQ ID NO:2;
   an EAA1c receptor wherein the polynucleotide coding therefor includes nucleotides 216 to 3023 of SEQ ID NO:1 or degenerate codon equivalents thereof, in which nucleotides 1427–1450 are deleted and the codon at positions 1737–1739 encodes isoleucine; and
   an EAA1d receptor, wherein the polynucleotide coding therefor includes nucleotides 216–3023 of SEQ ID NO:1, or degenerate codon equivalents thereof, in which nucleotides 1412–1460 are replaced by SEQ ID NO:13.

2. A human EAA1 receptor protein according to claim 1, wherein said protein is an EAA1a receptor having the amino acid sequence of residues 1–936 of SEQ ID NO:2 with a valine residue at amino acid position 508.

3. A human EAA1 receptor protein according to claim 1, wherein said protein is an EAA1b receptor having the amino acid sequence of residues 1–936 of SEQ ID NO:2.

4. A human EAA1 receptor protein according to claim 1, wherein said protein is an EAA1c receptor wherein the polynucleotide coding therefor includes nucleotides 216 to 3023 of SEQ ID NO:1 or degenerate codon equivalents thereof, in which nucleotides 1427–1450 are deleted and the codon at positions 1737–1739 encodes isoleucine.

5. A human EAA1 receptor protein according to claim 1, wherein said protein is an EAA1d receptor, wherein the polynucleotide coding therefor includes nucleotides 216–3023 of SEQ ID NO:1, or degenerate codon equivalents thereof, in which nucleotides 1412–1460 are replaced by SEQ ID NO:13.

* * * * *

SEQUENCE LISTING (1) GENERAL INFORMATION:

(iii) NUMBER OF SEQUENCES: 17

(2) INFORMATION FOR SEQ ID NO:1:

-continued

```
    (i) SEQUENCE CHARACTERISTICS:
        (A) LENGTH: 3708 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 156..3026

(ix) FEATURE:
        (A) NAME/KEY: sig_peptide
        (B) LOCATION: 156..215

(ix) FEATURE:
        (A) NAME/KEY: mat_peptide
        (B) LOCATION: 216..3026

(xi) SEQUENCE DESCRIPTION: SEQ ID NO:1:
```

| | |
|---|---|
| GAATTCCCTG AGTGCCTACT ATGTGCCAGC CTGTGCTAGG CACTGAGGAC ACAGGTGGAA | 60 |
| AAGCCCGAAT TGCTCCCTGC TCTCCTGGCG CTCATCACCC CGGAGAGTTA TGTCATGCCC | 120 |
| AGGCCAGCAG GGGGCTCCAT GAGGATTCAT AGAAG ATG CCC CGC GTC TCG GCG | 173 |
|                                           Met Pro Arg Val Ser Ala<br>                                          -20            -15 | |
| CCT TTG GTG CTG CTT CCT GCG TGG CTC GTG ATG GTC GCC TGC AGC CCG<br>Pro Leu Val Leu Leu Pro Ala Trp Leu Val Met Val Ala Cys Ser Pro<br>         -10                  -5                           1 | 221 |
| CAC TCC TTG AGG ATC GCT GCT ATC TTG GAC GAC CCC ATG GAG TGC AGC<br>His Ser Leu Arg Ile Ala Ala Ile Leu Asp Asp Pro Met Glu Cys Ser<br>     5                     10                    15 | 269 |
| AGA GGG GAG CGG CTC TCC ATC ACC CTG GCC AAG AAC CGC ATC AAC CGC<br>Arg Gly Glu Arg Leu Ser Ile Thr Leu Ala Lys Asn Arg Ile Asn Arg<br> 20                    25                    30 | 317 |
| GCT CCT GAG AGG CTG GGC AAG GCC AAG GTC GAA GTG GAC ATC TTT GAG<br>Ala Pro Glu Arg Leu Gly Lys Ala Lys Val Glu Val Asp Ile Phe Glu<br> 35                    40                   45                 50 | 365 |
| CTT CTC AGA GAC AGC GAG TAC GAG ACT GCA GAA ACC ATG TGT CAG ATC<br>Leu Leu Arg Asp Ser Glu Tyr Glu Thr Ala Glu Thr Met Cys Gln Ile<br>            55                    60                    65 | 413 |
| CTC CCC AAG GGG GTG GTC GCT GTC CTC GGA CCA TCG TCC AGC CCA GCC<br>Leu Pro Lys Gly Val Val Ala Val Leu Gly Pro Ser Ser Ser Pro Ala<br>               70                    75                    80 | 461 |
| TCC AGC TCC ATC ATC AGC AAC ATC TGT GGA GAG AAG GAG GTC CCT CAC<br>Ser Ser Ser Ile Ile Ser Asn Ile Cys Gly Glu Lys Glu Val Pro His<br>            85                    90                    95 | 509 |
| TTC AAA GTG GCC CCA GAG GAG TTC GTC AAG TTC CAG TTC CAG AGA TTC<br>Phe Lys Val Ala Pro Glu Glu Phe Val Lys Phe Gln Phe Gln Arg Phe<br> 100                       105                   110 | 557 |
| ACA ACC CTG AAC CTC CAC CCC AGC AAC ACT GAC ATC AGC GTG GCT GTA<br>Thr Thr Leu Asn Leu His Pro Ser Asn Thr Asp Ile Ser Val Ala Val<br>115                  120                    125                  130 | 605 |
| GCT GGG ATC CTG AAC TTC TTC AAC TGC ACC ACC GCC TGC CTC ATC TGT<br>Ala Gly Ile Leu Asn Phe Phe Asn Cys Thr Thr Ala Cys Leu Ile Cys<br>               135                    140                    145 | 653 |
| GCC AAA GCA GAA TGC CTT TTA AAC CTA GAG AAG CTG CTC CGG CAA TTC<br>Ala Lys Ala Glu Cys Leu Leu Asn Leu Glu Lys Leu Leu Arg Gln Phe<br>            150                    155                    160 | 701 |
| CTT ATC TCC AAG GAC ACG CTG TCC GTC CGC ATG CTG GAT GAC ACC CGG<br>Leu Ile Ser Lys Asp Thr Leu Ser Val Arg Met Leu Asp Asp Thr Arg<br>               165                    170                    175 | 749 |
| GAC CCC ACC CCG CTC CTC AAG GAG ATC CGG GAC GAC AAG ACC GCC ACC<br>Asp Pro Thr Pro Leu Leu Lys Glu Ile Arg Asp Asp Lys Thr Ala Thr | 797 |

```
              180                 185                 190
ATC ATC ATC CAC GCC AAC GCC TCC ATG TCC CAC ACC ATC CTC CTG AAG        845
Ile Ile Ile His Ala Asn Ala Ser Met Ser His Thr Ile Leu Leu Lys
195                 200                 205                 210

GCA GCC GAA CTT GGG ATG GTG TCA GCC TAT TAC ACA TAC ATC TTC ACT        893
Ala Ala Glu Leu Gly Met Val Ser Ala Tyr Tyr Thr Tyr Ile Phe Thr
                215                 220                 225

AAT CTG GAG TTC TCA CTC CAG AGA ACG GAC AGC CTT GTG GAT GAT CGT        941
Asn Leu Glu Phe Ser Leu Gln Arg Thr Asp Ser Leu Val Asp Asp Arg
                230                 235                 240

GTC AAC ATC CTG GGA TTT TCC ATT TTC AAC CAA TCC CAT GCT TTC TTC        989
Val Asn Ile Leu Gly Phe Ser Ile Phe Asn Gln Ser His Ala Phe Phe
            245                 250                 255

CAA GAG TTT GCC CAG AGC CTC AAC CAG TCC TGG CAG GAG AAC TGT GAC       1037
Gln Glu Phe Ala Gln Ser Leu Asn Gln Ser Trp Gln Glu Asn Cys Asp
        260                 265                 270

CAT GTG CCC TTC ACT GGG CCT GCG CTC TCC TCG GCC CTG CTG TTT GAT       1085
His Val Pro Phe Thr Gly Pro Ala Leu Ser Ser Ala Leu Leu Phe Asp
275                 280                 285                 290

GCT GTC TAT GCT GTG GTG ACT GCG GTG CAG GAA CTG AAC CGG AGC CAA       1133
Ala Val Tyr Ala Val Val Thr Ala Val Gln Glu Leu Asn Arg Ser Gln
                295                 300                 305

GAG ATC GGC GTG AAG CCC TTG TCC TGC GGC TCG GCC CAG ATC TGG CAG       1181
Glu Ile Gly Val Lys Pro Leu Ser Cys Gly Ser Ala Gln Ile Trp Gln
                310                 315                 320

CAC GGC ACC AGC CTC ATG AAC TAC CTG CGC ATG GTA GAA TTG GAA GGT       1229
His Gly Thr Ser Leu Met Asn Tyr Leu Arg Met Val Glu Leu Glu Gly
            325                 330                 335

CTT ACC GGC CAC ATT GAA TTC AAC AGC AAA GGC CAG AGG TCC AAC TAC       1277
Leu Thr Gly His Ile Glu Phe Asn Ser Lys Gly Gln Arg Ser Asn Tyr
        340                 345                 350

GCT TTG AAA ATC TTA CAG TTC ACA AGG AAT GGT TTT CGG CAG ATC GGC       1325
Ala Leu Lys Ile Leu Gln Phe Thr Arg Asn Gly Phe Arg Gln Ile Gly
355                 360                 365                 370

CAG TGG CAC GTG GCA GAG GGC CTC AGC ATG GAC AGC CAC CTC TAT GCC       1373
Gln Trp His Val Ala Glu Gly Leu Ser Met Asp Ser His Leu Tyr Ala
                375                 380                 385

TCC AAC ATC TCG GAC ACT CTC TTC AAC ACC ACC CTG GTC GTC ACC ACC       1421
Ser Asn Ile Ser Asp Thr Leu Phe Asn Thr Thr Leu Val Val Thr Thr
                390                 395                 400

ATC CTG GAA AAC CCA TAT TTA ATG CTG AAG GGG AAC CAC CAG GAG ATG       1469
Ile Leu Glu Asn Pro Tyr Leu Met Leu Lys Gly Asn His Gln Glu Met
            405                 410                 415

GAA GGC AAT GAC CGC TAC GAG GGC TTC TGT GTG GAC ATG CTC AAG GAG       1517
Glu Gly Asn Asp Arg Tyr Glu Gly Phe Cys Val Asp Met Leu Lys Glu
        420                 425                 430

CTG GCA GAG ATC CTC CGA TTC AAC TAC AAG ATC CGC CTG GTT GGG GAT       1565
Leu Ala Glu Ile Leu Arg Phe Asn Tyr Lys Ile Arg Leu Val Gly Asp
435                 440                 445                 450

GGC GTG TAC GGC GTT CCC GAG GCC AAC GGC ACC TGG ACG GGA ATG GTC       1613
Gly Val Tyr Gly Val Pro Glu Ala Asn Gly Thr Trp Thr Gly Met Val
                455                 460                 465

GGG GAG CTG ATC GCT AGG AAA GCA GAT CTG GCT GTG GCA GGC CTC ACC       1661
Gly Glu Leu Ile Ala Arg Lys Ala Asp Leu Ala Val Ala Gly Leu Thr
                470                 475                 480

ATT ACA GCT GAA CGG GAG AAG GTG ATT GAT TTC TCT AAG CCA TTC ATG       1709
Ile Thr Ala Glu Arg Glu Lys Val Ile Asp Phe Ser Lys Pro Phe Met
            485                 490                 495

ACT CTG GGA ATT AGC ATT CTT TAC CGC ATT CAT ATG GGA CGC AAA CCC       1757
Thr Leu Gly Ile Ser Ile Leu Tyr Arg Ile His Met Gly Arg Lys Pro
```

-continued

```
       500                 505                 510
GGC TAT TTC TCC TTC CTG GAC CCA TTT TCT CCG GGC GTC TGG CTC TTC        1805
Gly Tyr Phe Ser Phe Leu Asp Pro Phe Ser Pro Gly Val Trp Leu Phe
515                 520                 525                 530

ATG CTT CTA GCC TAT CTG GCC GTC AGC TGT GTC CTC TTC CTG GTG GCT        1853
Met Leu Leu Ala Tyr Leu Ala Val Ser Cys Val Leu Phe Leu Val Ala
                535                 540                 545

CGG TTG ACG CCC TAC GAG TGG TAC AGC CCA CAC CCA TGT GCC CAG GGC        1901
Arg Leu Thr Pro Tyr Glu Trp Tyr Ser Pro His Pro Cys Ala Gln Gly
                550                 555                 560

CGG TGC AAC CTC CTG GTG AAC CAG TAC TCC CTG GGC AAC AGC CTC TGG        1949
Arg Cys Asn Leu Leu Val Asn Gln Tyr Ser Leu Gly Asn Ser Leu Trp
        565                 570                 575

TTT CCG GTC GGG GGG TTC ATG CAG CAG GGC TCC ACC ATC GCC CCT CGC        1997
Phe Pro Val Gly Gly Phe Met Gln Gln Gly Ser Thr Ile Ala Pro Arg
        580                 585                 590

GCC TTA TCC ACC CGC TGT GTC AGT GGC GTC TGG TGG GCA TTC ACG CTG        2045
Ala Leu Ser Thr Arg Cys Val Ser Gly Val Trp Trp Ala Phe Thr Leu
595                 600                 605                 610

ATC ATC ATC TCA TCC TAC ACG GCC AAC CTG GCA GCC TTC CTG ACC GTG        2093
Ile Ile Ile Ser Ser Tyr Thr Ala Asn Leu Ala Ala Phe Leu Thr Val
                615                 620                 625

CAG CGC ATG GAT GTG CCC ATT GAG TCA GTG GAT GAC CTG GCT GAC CAG        2141
Gln Arg Met Asp Val Pro Ile Glu Ser Val Asp Asp Leu Ala Asp Gln
                630                 635                 640

ACC GCC ATT GAA TAT GGC ACA ATT CAC GGA GGC TCC AGC ATG ACC TTC        2189
Thr Ala Ile Glu Tyr Gly Thr Ile His Gly Gly Ser Ser Met Thr Phe
                645                 650                 655

TTC CAA AAT TCC CGC TAC CAG ACC TAC CAA CGC ATG TGG AAT TAC ATG        2237
Phe Gln Asn Ser Arg Tyr Gln Thr Tyr Gln Arg Met Trp Asn Tyr Met
        660                 665                 670

TAT TCC AAG CAG CCC AGC GTG TTC GTG AAG AGC ACA GAG GAG GGA ATC        2285
Tyr Ser Lys Gln Pro Ser Val Phe Val Lys Ser Thr Glu Glu Gly Ile
675                 680                 685                 690

GCC AGG GTG TTG AAT TCC AAC TAC GCC TTC CTC CTG GAA TCC ACC ATG        2333
Ala Arg Val Leu Asn Ser Asn Tyr Ala Phe Leu Leu Glu Ser Thr Met
                695                 700                 705

AAC GAG TAC TAT CGG CAG CGA AAC TGC AAC CTC ACT CAG ATT GGG GGC        2381
Asn Glu Tyr Tyr Arg Gln Arg Asn Cys Asn Leu Thr Gln Ile Gly Gly
                710                 715                 720

CTG CTG GAC ACC AAG GGC TAT GGG ATT GGC ATG CCA GTC GGC TCG GTT        2429
Leu Leu Asp Thr Lys Gly Tyr Gly Ile Gly Met Pro Val Gly Ser Val
                725                 730                 735

TTC CGG GAC GAG TTT GAT CTG GCC ATT CTC CAG CTG CAG GAG AAC AAC        2477
Phe Arg Asp Glu Phe Asp Leu Ala Ile Leu Gln Leu Gln Glu Asn Asn
        740                 745                 750

CGC CTG GAG ATC CTG AAG CGC AAA TGG TGG GAA GGA GGG AAG TGC CCC        2525
Arg Leu Glu Ile Leu Lys Arg Lys Trp Trp Glu Gly Gly Lys Cys Pro
755                 760                 765                 770

AAG GAG GAA GAT CAC AGA GCT AAA GGC CTG GGA ATG GAG AAT ATT GGT        2573
Lys Glu Glu Asp His Arg Ala Lys Gly Leu Gly Met Glu Asn Ile Gly
                775                 780                 785

GGA ATC TTT GTG GTT CTT ATT TGT GGC TTA ATC GTG GCC ATT TTT ATG        2621
Gly Ile Phe Val Val Leu Ile Cys Gly Leu Ile Val Ala Ile Phe Met
                790                 795                 800

GCT ATG TTG GAG TTT TTA TGG ACT CTC AGA CAC TCA GAA GCA ACT GAG        2669
Ala Met Leu Glu Phe Leu Trp Thr Leu Arg His Ser Glu Ala Thr Glu
                805                 810                 815

GTG TCC GTC TGC CAG GAG ATG GTG ACC GAG CTG CGC AGC ATT ATC CTG        2717
Val Ser Val Cys Gln Glu Met Val Thr Glu Leu Arg Ser Ile Ile Leu
```

```
                820                825                830
TGT CAG GAC AGT ATC CAC CCC CGC CGG CGG CGC GCC GCA GTC CCG CCG    2765
Cys Gln Asp Ser Ile His Pro Arg Arg Arg Arg Ala Ala Val Pro Pro
835                 840                845                850

CCC CGG CCC CCC ATC CCC GAG GAG CGC CGA CCG CGG GGC ACG GCG ACG    2813
Pro Arg Pro Pro Ile Pro Glu Glu Arg Arg Pro Arg Gly Thr Ala Thr
                855                860                865

CTC AGC AAC GGG AAG CTG TGC GGG GCA GGG GAG CCC GAC CAG CTC GCG    2861
Leu Ser Asn Gly Lys Leu Cys Gly Ala Gly Glu Pro Asp Gln Leu Ala
            870                875                880

CAG AGA CTG GCG CAG GAG GCC GCC CTG GTG GCC CGC GGC TGC ACG CAC    2909
Gln Arg Leu Ala Gln Glu Ala Ala Leu Val Ala Arg Gly Cys Thr His
        885                890                895

ATC CGC GTC TGC CCC GAG TGC CGC CGC TTC CAG GGC CTG CGG GCA CGG    2957
Ile Arg Val Cys Pro Glu Cys Arg Arg Phe Gln Gly Leu Arg Ala Arg
    900                905                910

CCG TCG CCC GCC CGC AGC GAG GAG AGC CTG GAG TGG GAG AAA ACC ACC    3005
Pro Ser Pro Ala Arg Ser Glu Glu Ser Leu Glu Trp Glu Lys Thr Thr
915                920                925                930

AAC AGC AGC GAG CCC GAG TAGTCCCGGA GGCCACAGGA CGCGCAGAGG           3053
Asn Ser Ser Glu Pro Glu
                935

CCGGGCGGGG CGGGAGGGGA GGGGCGGGGC GGGCGCTGCT GTCAGCCGCC AGCCGGAACT  3113

TGTACAGCGT CGACACCTCT CCAGATTTCG GATCCAGTCA CTTTTCAAAA AGATCAAGGA  3173

GCCTGACGCC CCAGCCAGAG ACCGCGCCCG GTCAGGGAGC AGGGTCCACC CGGAAACGTT  3233

GCACCCAAAG GGCAAAGGAC GGCCCTCCCT CCTGGGCACA AGGACCCATC TTCTCCCAGT  3293

GGGTCTTTCC CTCTCGCCAA AATAACAAGA GTATAGGGTG GGGGGTCCCT ACCCAGACCA  3353

GTCCAATGAA TTGGTGGAAT CATCAGTTGA ATTTCCCCCT AGTCAGGGGC CAATGTACCC  3413

TCCGTCTAGT TCTTACAGAA AAAAAAAAAA ATTAAACAGG GAAGTTTTTC TTTTCTGGAT  3473

TTGTATATTT TTGTTAATGT TCTTTTCCCT TTTCTTTCCT CCTCTCCTTT TCTTCTTTGT  3533

CATCTTCTCA GTCCTGTTAA TTTGTTTTGT GTTTTTTGGA GGGGGAGGCT GGGTTAGGGA  3593

ATGGAAGCCT AAATAATCCC TATTTCTTCT TTTTCCTGAA TTTTGGAATA TTGCGTTACC  3653

AGTGCATCCG ATTTCAGGTG CGGAACTCTC TGTATGGTGA CTGAGGGGCC TGCAG       3708

(2) INFORMATION FOR SEQ ID NO:2:

(i) SEQUENCE CHARACTERISTICS:
        (A) LENGTH: 956 amino acids
        (B) TYPE: amino acid
        (D) TOPOLOGY: linear (ii) MOLECULE TYPE: protein (xi) SEQUENCE DESCRIPTION: SEQ ID NO:2:

Met Pro Arg Val Ser Ala Pro Leu Val Leu Leu Pro Ala Trp Leu Val
-20                 -15                -10                -5

Met Val Ala Cys Ser Pro His Ser Leu Arg Ile Ala Ala Ile Leu Asp
                1               5                  10

Asp Pro Met Glu Cys Ser Arg Gly Glu Arg Leu Ser Ile Thr Leu Ala
            15              20                 25

Lys Asn Arg Ile Asn Arg Ala Pro Glu Arg Leu Gly Lys Ala Lys Val
        30              35                 40

Glu Val Asp Ile Phe Glu Leu Leu Arg Asp Ser Glu Tyr Glu Thr Ala
45              50                 55                 60

Glu Thr Met Cys Gln Ile Leu Pro Lys Gly Val Val Ala Val Leu Gly
```

```
                    65                  70                  75
Pro Ser Ser Ser Pro Ala Ser Ser Ile Ile Ser Asn Ile Cys Gly
                80                  85                  90
Glu Lys Glu Val Pro His Phe Lys Val Ala Pro Glu Glu Phe Val Lys
            95                 100                 105
Phe Gln Phe Gln Arg Phe Thr Thr Leu Asn Leu His Pro Ser Asn Thr
        110                 115                 120
Asp Ile Ser Val Ala Val Ala Gly Ile Leu Asn Phe Phe Asn Cys Thr
125                 130                 135                 140
Thr Ala Cys Leu Ile Cys Ala Lys Ala Glu Cys Leu Leu Asn Leu Glu
                145                 150                 155
Lys Leu Leu Arg Gln Phe Leu Ile Ser Lys Asp Thr Leu Ser Val Arg
            160                 165                 170
Met Leu Asp Asp Thr Arg Asp Pro Thr Pro Leu Leu Lys Glu Ile Arg
        175                 180                 185
Asp Asp Lys Thr Ala Thr Ile Ile His Ala Asn Ala Ser Met Ser
190                 195                 200
His Thr Ile Leu Leu Lys Ala Ala Glu Leu Gly Met Val Ser Ala Tyr
205                 210                 215                 220
Tyr Thr Tyr Ile Phe Thr Asn Leu Glu Phe Ser Leu Gln Arg Thr Asp
                225                 230                 235
Ser Leu Val Asp Asp Arg Val Asn Ile Leu Gly Phe Ser Ile Phe Asn
            240                 245                 250
Gln Ser His Ala Phe Phe Gln Glu Phe Ala Gln Ser Leu Asn Gln Ser
        255                 260                 265
Trp Gln Glu Asn Cys Asp His Val Pro Phe Thr Gly Pro Ala Leu Ser
    270                 275                 280
Ser Ala Leu Leu Phe Asp Ala Val Tyr Ala Val Val Thr Ala Val Gln
285                 290                 295                 300
Glu Leu Asn Arg Ser Gln Glu Ile Gly Val Lys Pro Leu Ser Cys Gly
                305                 310                 315
Ser Ala Gln Ile Trp Gln His Gly Thr Ser Leu Met Asn Tyr Leu Arg
            320                 325                 330
Met Val Glu Leu Glu Gly Leu Thr Gly His Ile Glu Phe Asn Ser Lys
        335                 340                 345
Gly Gln Arg Ser Asn Tyr Ala Leu Lys Ile Leu Gln Phe Thr Arg Asn
    350                 355                 360
Gly Phe Arg Gln Ile Gly Gln Trp His Val Ala Glu Gly Leu Ser Met
365                 370                 375                 380
Asp Ser His Leu Tyr Ala Ser Asn Ile Ser Asp Thr Leu Phe Asn Thr
                385                 390                 395
Thr Leu Val Val Thr Thr Ile Leu Glu Asn Pro Tyr Leu Met Leu Lys
            400                 405                 410
Gly Asn His Gln Glu Met Glu Gly Asn Asp Arg Tyr Glu Gly Phe Cys
        415                 420                 425
Val Asp Met Leu Lys Glu Leu Ala Glu Ile Leu Arg Phe Asn Tyr Lys
    430                 435                 440
Ile Arg Leu Val Gly Asp Gly Val Tyr Gly Val Pro Glu Ala Asn Gly
445                 450                 455                 460
Thr Trp Thr Gly Met Val Gly Glu Leu Ile Ala Arg Lys Ala Asp Leu
                465                 470                 475
Ala Val Ala Gly Leu Thr Ile Thr Ala Glu Arg Glu Lys Val Ile Asp
            480                 485                 490
```

-continued

```
Phe Ser Lys Pro Phe Met Thr Leu Gly Ile Ser Ile Leu Tyr Arg Ile
        495                 500                 505

His Met Gly Arg Lys Pro Gly Tyr Phe Ser Phe Leu Asp Pro Phe Ser
        510                 515                 520

Pro Gly Val Trp Leu Phe Met Leu Leu Ala Tyr Leu Ala Val Ser Cys
525                 530                 535                 540

Val Leu Phe Leu Val Ala Arg Leu Thr Pro Tyr Glu Trp Tyr Ser Pro
                545                 550                 555

His Pro Cys Ala Gln Gly Arg Cys Asn Leu Leu Val Asn Gln Tyr Ser
        560                 565                 570

Leu Gly Asn Ser Leu Trp Phe Pro Val Gly Gly Phe Met Gln Gln Gly
        575                 580                 585

Ser Thr Ile Ala Pro Arg Ala Leu Ser Thr Arg Cys Val Ser Gly Val
        590                 595                 600

Trp Trp Ala Phe Thr Leu Ile Ile Ile Ser Ser Tyr Thr Ala Asn Leu
605                 610                 615                 620

Ala Ala Phe Leu Thr Val Gln Arg Met Asp Val Pro Ile Glu Ser Val
                625                 630                 635

Asp Asp Leu Ala Asp Gln Thr Ala Ile Glu Tyr Gly Thr Ile His Gly
        640                 645                 650

Gly Ser Ser Met Thr Phe Phe Gln Asn Ser Arg Tyr Gln Thr Tyr Gln
        655                 660                 665

Arg Met Trp Asn Tyr Met Tyr Ser Lys Gln Pro Ser Val Phe Val Lys
        670                 675                 680

Ser Thr Glu Glu Gly Ile Ala Arg Val Leu Asn Ser Asn Tyr Ala Phe
685                 690                 695                 700

Leu Leu Glu Ser Thr Met Asn Glu Tyr Tyr Arg Gln Arg Asn Cys Asn
                705                 710                 715

Leu Thr Gln Ile Gly Gly Leu Leu Asp Thr Lys Gly Tyr Gly Ile Gly
        720                 725                 730

Met Pro Val Gly Ser Val Phe Arg Asp Glu Phe Asp Leu Ala Ile Leu
        735                 740                 745

Gln Leu Gln Glu Asn Asn Arg Leu Glu Ile Leu Lys Arg Lys Trp Trp
        750                 755                 760

Glu Gly Gly Lys Cys Pro Lys Glu Glu Asp His Arg Ala Lys Gly Leu
765                 770                 775                 780

Gly Met Glu Asn Ile Gly Gly Ile Phe Val Val Leu Ile Cys Gly Leu
                785                 790                 795

Ile Val Ala Ile Phe Met Ala Met Leu Glu Phe Leu Trp Thr Leu Arg
        800                 805                 810

His Ser Glu Ala Thr Glu Val Ser Val Cys Gln Glu Met Val Thr Glu
        815                 820                 825

Leu Arg Ser Ile Ile Leu Cys Gln Asp Ser Ile His Pro Arg Arg
        830                 835                 840

Arg Ala Ala Val Pro Pro Pro Arg Pro Ile Pro Glu Glu Arg Arg
845                 850                 855                 860

Pro Arg Gly Thr Ala Thr Leu Ser Asn Gly Lys Leu Cys Gly Ala Gly
                865                 870                 875

Glu Pro Asp Gln Leu Ala Gln Arg Leu Ala Gln Glu Ala Ala Leu Val
        880                 885                 890

Ala Arg Gly Cys Thr His Ile Arg Val Cys Pro Glu Cys Arg Arg Phe
        895                 900                 905

Gln Gly Leu Arg Ala Arg Pro Ser Pro Ala Arg Ser Glu Glu Ser Leu
        910                 915                 920
```

```
Glu Trp Glu Lys Thr Thr Asn Ser Ser Glu Pro Glu
925                 930                 935
```

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:3:

GGGGTTTAAG CTTCTGAGTG CCTACTATGT GCCCAG        36

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:4:

GGGTGGGGTC CCGGGTGTCA TC        22

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:5:

GATGACACCC GGGACCCCAC CC        22

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:6:

TGCGTCCCAT ATGAATGCGG TA        22

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:7:

TACCGCATTC ATATGGGACG CA                                    22

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:8:

GAGGTGTCGA CGCTGTACAA GT                                    22

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:9:

ACTTGTACAG CGTCGACACC TC                                    22

(2) INFORMATION FOR SEQ ID NO:10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:10:

GGGGTTTAAG CTTTACCACT GACTCCCCGG ACGTC                      35

(2) INFORMATION FOR SEQ ID NO:11:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:11:

AGCTTGCGGC CGC                                              13

(2) INFORMATION FOR SEQ ID NO:12:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (iv) ANTI-SENSE: YES (xi) SEQUENCE DESCRIPTION: SEQ ID NO:12:

GCGGCCGCA                                                                                       9

(2) INFORMATION FOR SEQ ID NO:13:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CGTCACCACC ATCCTGTTTT GCTGCAGGAA AACCCATATT TAATGCTGAA GGGGAACCAC          60

(2) INFORMATION FOR SEQ ID NO:14:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGTCACCACC ATCCTGGAAA ACCCATATTT AATGCTGAAG GGGAACCAC                     49

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CGTCACCACC ATCCTGGGGA ACCAC                                               25

(2) INFORMATION FOR SEQ ID NO:16:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other nucleic acid;
         (A) DESCRIPTION: Synthetic DNA oligonucleotide (xi) SEQUENCE DESCRIPTION: SEQ ID NO:16:

GGGGTTTAAG CTTGAGCGTC GTCCTCTTCC TGGT                                     34

(2) INFORMATION FOR SEQ ID NO:17:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other nucleic acid;
    (A) DESCRIPTION: Synthetic DNA oligonucleotide (xi) SEQUENCE DESCRIPTION: SEQ ID NO:17:

GGGGTTTAAG CTTGTGAAGA ACCACCAGAC GCCG                                34